United States Patent [19]
Nakamura

[11] Patent Number: 5,607,303
[45] Date of Patent: Mar. 4, 1997

[54] ACCESSORY APPARATUS OF DENTISTRY DRILLS FOR PUTTING ORAL CAVITY ORGANS OUT OF WAY

[76] Inventor: Shoukou Nakamura, 61-2 Tsurukouji-machi,, Maebashi-shi, Gunma, Japan

[21] Appl. No.: 285,646

[22] Filed: Aug. 3, 1994

[51] Int. Cl.$^6$ .................................................. A61C 5/00
[52] U.S. Cl. ........................................ 433/140; 433/116
[58] Field of Search .................................. 433/140, 116, 433/114

[56] References Cited

U.S. PATENT DOCUMENTS

| | | | |
|---|---|---|---|
| 1,285,273 | 11/1918 | Luzzi | 433/116 |
| 1,841,915 | 1/1932 | Reiter | 433/116 |
| 2,671,269 | 3/1954 | Francis | 433/116 |
| 4,611,992 | 9/1986 | Lokken | 433/116 |
| 4,701,128 | 10/1987 | Fitzig et al. | 433/116 |
| 5,052,924 | 10/1991 | Berg | 433/114 |
| 5,163,842 | 11/1992 | Nonomura | 433/114 |
| 5,178,536 | 1/1993 | Werly et al. | 433/114 |
| 5,306,148 | 4/1994 | Nakamura | 433/116 |

FOREIGN PATENT DOCUMENTS

| | | | |
|---|---|---|---|
| 2140308 | 11/1984 | United Kingdom | 433/140 |

*Primary Examiner*—Edgar S. Burr
*Assistant Examiner*—Anthony H. Nguyen
*Attorney, Agent, or Firm*—Koda and Androlia

[57] ABSTRACT

This invention relates to a new displacement equipment installed in air-turbine or contra dentistry drilling machines, used by the dentist in cutting treatment. By installing the equipment of this invention at the base of common cutting machines, the dentist can move the cutting machine while removing oral cavity organs when necessary with one-hand finger operations, during utilization inside the oral cavity. It is basically formed by the installation member with hole, through which the base of the dentistry drilling machine is inserted and is fixed in a constant position, by the arm installed in the supporting hole of the installation member, and by the displacement plate, installed on the tip of the arm. The arm, installed on the tip of the displacement plate, is formed by many arms number which can rotate in the horizontal and vertical directions according to the user's finger articulations. The function of the tip of the tip arm, which can move in the vertical direction, is to form the shape of the tip of the instrument to be inserted into the oral organ. The function of the medium arm and others is to hold the oral cavity organs located on the side of the tool, such as lips, tongue, masseter, lower maxilla lower protuberance, etc. Furthermore, by constructing it so that the installation member does not separate from the cutting machine, and permitting the cutting machine to freely rotate around the axis, or by installing the installation member in the cutting machine so as to allow floating, it is possible to apply a strong pressure with the tip of the arm or the displacement plate with any finger to hold oral cavity organs during operation inside the oral cavity, while handling the cutting machine freely with other fingers.

6 Claims, 54 Drawing Sheets

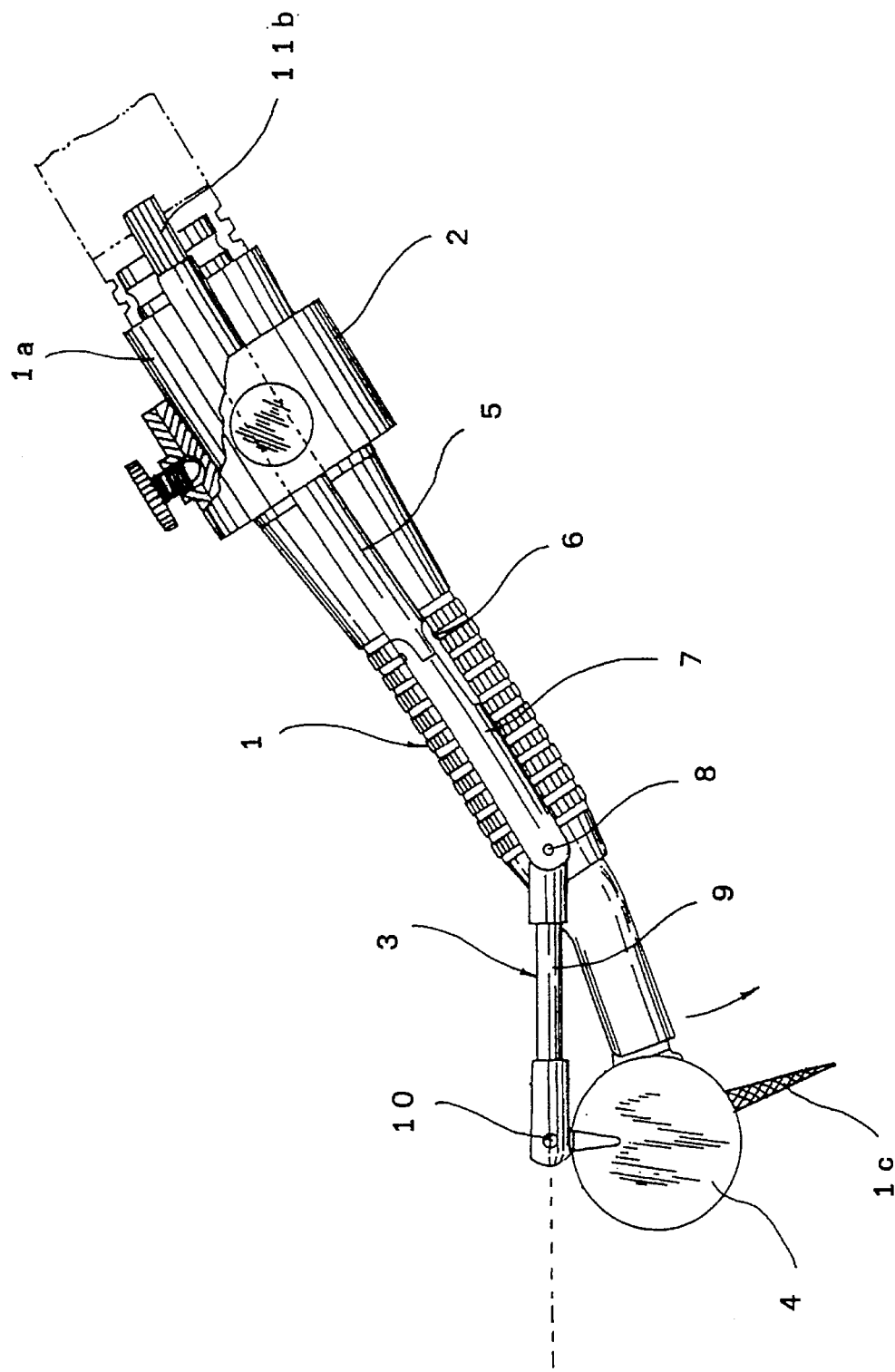

ACCESSORY APPARATUS OF DENTISTRY DRILLS FOR PUTTING ORAL CAVITY ORGANS OUT OF WAY

BACKGROUND OF THE INVENTION

1. Field of the Invention

This invention relates to a new apparatus to be installed in dentistry drill such as air turbines or contras, used for dentistry treatment, for putting oral cavity organs out of way.

2. Description of the Prior Art

In general, medical instruments such as drilling machines with a cutting tool (bur) on the tip, mirrors for observing the state of the location being submitted to treatment, and vacuum tips to remove waste fluids such as saliva are utilized for dental treatment involving drilling and other kinds of operation. Among these various tools, mirror and vacuum tip are also used to put oral cavity organs, such as lips, tongue, cheeks, masseter, upper and lower protruding maxillary muscles, etc., that interfere with treatment, and thus avoid contact with the cutting tool (bur).

However, it is difficult for the dentist to utilize these various apparatuses all by himself. Specialized assistants, that take care of the compressive displacement job, that consists of putting the oral cavity organs that interfere with the treatment work out of the way by holding them by means of such apparatuses as the mirror, the vacuum tip or the hand, are required.

Therefore, in these types of drilling treatment, the so-called "four-handed dentistry", where the patient laying on his back is submitted to the treatment carried out by the dentist and the assistant, is the most common treatment position. In this case, such skilled techinques as mirror and oral vacuum techniques and techniques for handing over of tools are necessary for both the dentist and the assistant. Besides that, if there is considerable difference between the skill levels of the dentist and the assistant, there is possibility of occurrence of such problems as the treatment may not be carried out smoothly, it may take too much time, etc.

The "four-handed dentistry" carried out in the sitting position, which was discussed above, is extremely advantageous for executing complex works, such as those required in surgeries. It must be remembered, however, that most of the dental treatments are related to caries and the drilling treatments related the teeth. This invention, which is a new dentistry apparatus, was developed in view of such a reality and the problems mentioned above, in order to make it possible for the dentist to easily execute the drilling treatments by himself, at the various parts to be submitted the treatment.

The technical functions of the mirror and the vacuum tip used for putting the oral cavity organs out of the way in the drilling treatment of the teeth are: first, to avoid contact between the cutting tool (bur) and the oral cavity organs; second, to improve visibility of the cutting tool (bur), hindered by the oral cavity organs; third, to improve visibility of the part being submitted to treatment; and fourth, to make up room to freely move the cutting tool (bur) near the teeth. Regarding tools that satisfy mainly the first function, American U.S. Pat. Nos. 525,278, 1,004,118, 107,571, 1,101,947, 2,307,677, 2,671,269 and 2,924,013, among others, are drilling machine systems that have protecting plates on the tips. These protecting plates are installed in appropriate places near the tip of drilling machines, surrounding the cutting tool (bur) either partially or totally, to avoid contact between the cutting tool (bur) and the oral cavity organs.

However, the only objective of the protecting plate apparatuses shown in those patents is merely to protect oral cavity organs located at the periphery of the bur, and thus the position of the tip of the cutting machine either cannot be adjusted, or rotates just a little at the point of contact. It is then impossible to adjust the position during utilization inside the oral cavity. With respect to the cutting tool (bur), it is not built in such as to make it possible to put the oral cavity organs out of the way by compressing them. For that reason, it is obvious that it is necessary to use other apparatuses such as mirrors, vacuum tips and the like when utilizing this kind of apparatus. Furthermore, the visibility of the cutting tool (bur) becomes even worse with the installation of the protecting plate, thereby impeding the execution of an appropriate treatment in the teeth of the patient.

SUMMARY OF THE INVENTION

The objective of this invention is to present a new displacement equipment which when installed on the tip of conventional dentistry drilling machines, allows the dentist to use the drilling machine while putting oral cavity organs out of the way whenever necessary, with one-hand finger movements, during treatment inside the oral cavity.

This invention, as seen in the figures showing execution examples, is formed basically by the holding part 1a of the drilling machine 1, the installation member 2 with the installation hole 2a, which is introduced on the side of the tip and is fixed at any position, by the arm 3, which is installed in the installation member 2 and in the supporting hole 2b, and the displacement plate 4, installed at the end of the arm 3.

However, when using this type of apparatus inside the oral cavity, the lower maxilla is kept open in order to facilitate the introduction of the apparatus and its operation, but in this state the movement of the drilling machine is strongly limited by the shape of the oral cavity and the oral cavity organs. In other words, there are variations in the front yard depth of the oral cavity, besides the limitation that in the open-and-shut movement of the lower maxilla around the lower maxilla head, the space in the oral cavity decreases from the region in front of the lips to the inner part of the soft palate.

DESCRIPTION OF THE INVENTION

1. In this invention, among the components of the oral cavity organ displacement equipment mentioned above, arm 3 with displacement plate 4 installed at the tip was built by connecting various arms (for example, supporting arm 5, medium arm 7, tip arm 9) that can rotate horizontally and vertically at appropriate positions according to the movements of the articulations of the user's fingers, as shown in the first execution example, in FIGS. 1 through 5. Among them, the tip of tip arm 9 does not suffer the influence of the limitations, and its function is to form the shape of the tip of the tool that is inserted into the oral cavity. The function of the medium arm 7 and others, that move in the horizontal direction, is to put the lips, the tongue, the masseter and the lower maxilla muscle protuberance out of the way by compressing them.

The base of the arm 3 is installed in the base 1a through installation member 2 forming one body, not at the center or the tip of the drilling machine, and is placed at equal distances along the axis of the drilling machine 1. Due to this construction, the dentist can move the thumb or the forefinger and apply independent forces on the drilling machine 1 and the arm 3, by using the base of any of his hand's fingers or the middle finger to hold the installation member 2 and the arm 3 in a stable position.

Thus, the most important effect of this displacement equipment is that it enables the dentist to change the shape of the tip of the tool with movements of the fingers, so as to permit insertion into the narrow space deep inside the oral cavity, from the relatively large space in front of the oral cavity. Moreover, as shown in FIGS. 58 to 61, it enables the application of strong pressure on the tip of the arm 3 and on the displacement plate 4, during the operation of the treatment equipment inside the oral cavity, in order to put the oral cavity organs out of the way by compressing them, and at the same time, the drilling machine 1 can be freely handled with other fingers. In concrete terms, by using the pressure applied through the fingers on the tip of the arm 3, the oral cavity organs such as tongue and jaw can be compressed by means of the displacement plate 4, and the tip of drilling machine 1 can be utilized freely in the vertical or horizontal directions. During that process, since there is absolutely no concern that displacement plate 4 moves together with the tip of the drilling machine 1, this operation of the treatment equipment can be executed smoothly. As to the rotating movement, adjustment is necessary so that each arm is fixed at a specific angle.

2. In another execution example of this invention, the installation member 2 is not separated from the cutting machine, but is rather installed around the axis of the drilling machine 1, with free rotating movement. This is show in the second execution example of the displacement equipment, in FIGS. 23 to 36, or in execution example 9. According to this construction, besides the effect described above, while the oral cavity organs are held at appropriate positions with displacement plate 4 during the operation of the treatment equipment inside the oral cavity, the drilling machine 1 can be rotated around an axis, permitting ideal positioning of the edge of cutting tool (bur) 1c with respect to appropriate locations of the teeth, which are the object of the operation. Also in this case, the rotation of the drilling machine 1 does not influence the displacement plate 4 at all, and so it is possible to use the displacement plate 4 to hold the oral cavity organs. The arm 3, with the above-mentioned rotating mechanism, is utilized in the construction this displacement apparatus, but depending on the rotating operation of the machine 1, the displacement plate 4 can in fact move on one side of the drilling machine 1, in the vertical direction. Thus, during the insertion of the tool inside the oral cavity, there is the structural advantage that it permits elimination of the vertical rotating mechanism.

3. In another execution example of this invention, considering that the construction and manufacturing process of the arm with rotating mechanism mentioned above are complex, this construction was improved. In the new construction, the installation member 2 is loosely installed in the drilling machine 1, and the tip of the drilling machine 1 is built in such a way to permit free operation. They can be seen in the displacement equipment shown in FIGS. 37 to 49, in execution example 10, or in execution example 13.

In these displacement equipment constructions, the open-and-shut movement of arm 3 and machine 1 occurs mostly with the installation member 2 working as the fulcrum. Furthermore, since this fulcrum moves along the circular track of the drilling machine 1, the variation of the relative movements increase among the displacement plate 4, located at the end of arm 3, and the drilling tool (bur) 1c, on the tip of the drilling machine 1. As a consequence, since it is possible to use the arm 3, which does not have any rotating mechanism, the stability of displacement plate 4 is considerably improved, and the construction of the displacement equipment as a whole can be made simpler.

4. Furthermore, in each of the execution examples of this invention, while the displacement plate 4 and the arm 3 are connected through a rotating mechanism, a displacement plate 4 with a differently-shaped tongue 4a is proposed. Consequently, it is possible to choose the position and shape of displacement plate 4, according to the shape of the oral cavity organs.

BRIEF DESCRIPTION OF THE DRAWINGS

FIGS. 51 to 57 are the schematics explaining the movements of the dentistry drilling machine inside the oral cavity.

EXAMPLES

Figure 1:
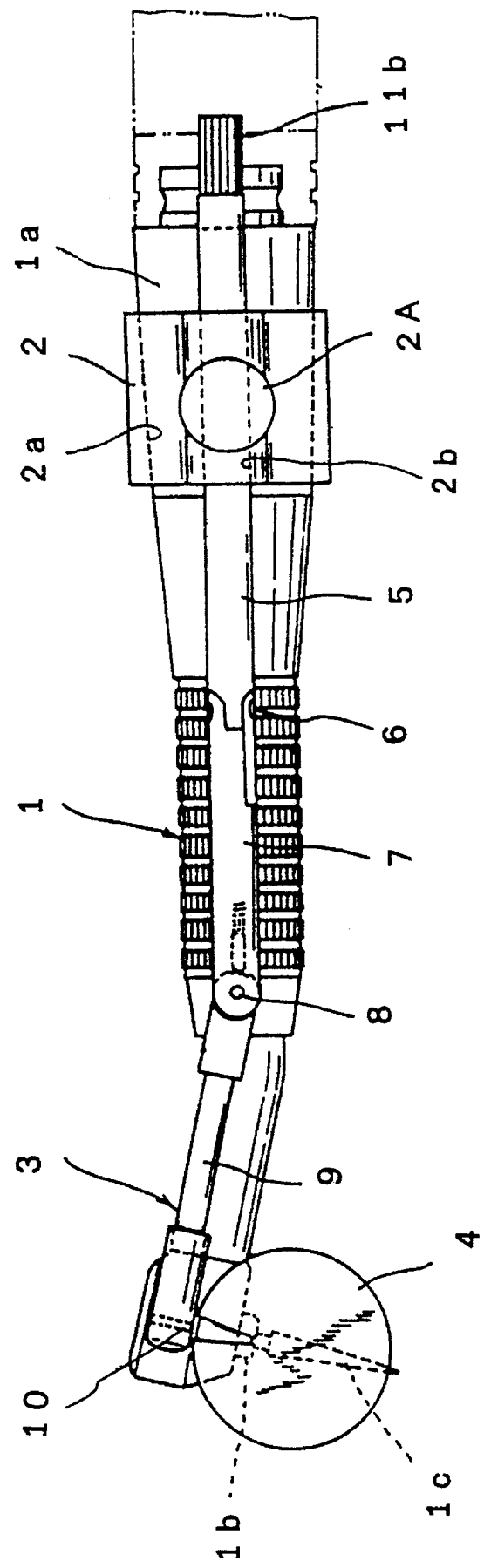
FIGS. 1 to 5 are the sketches of the displacement equipment of execution example 1.
Figure 2:
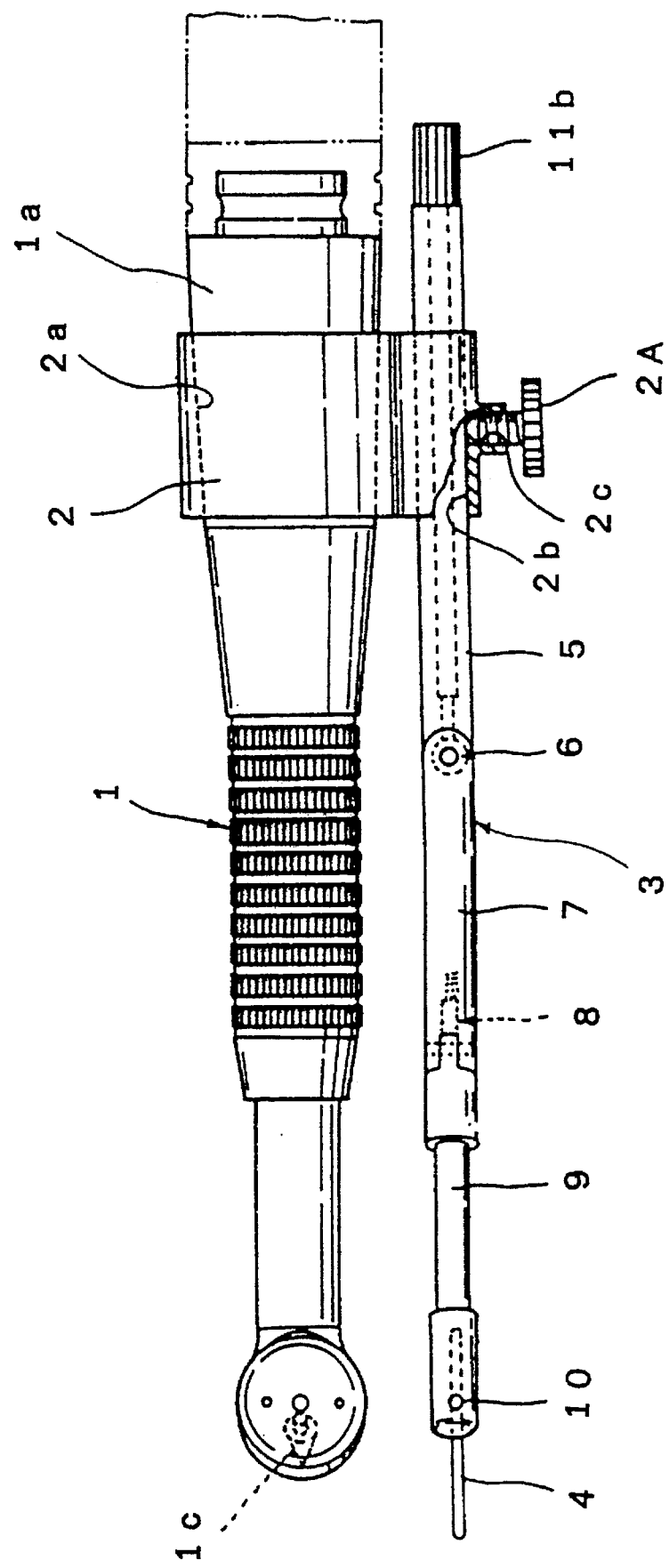
Figure 3:
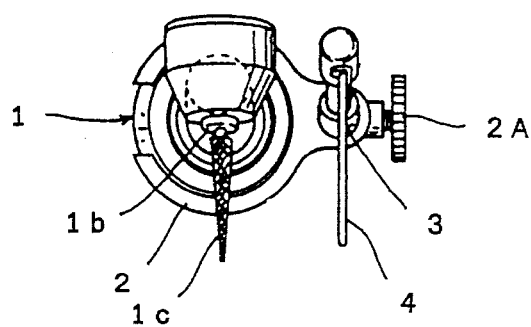
Figure 4:
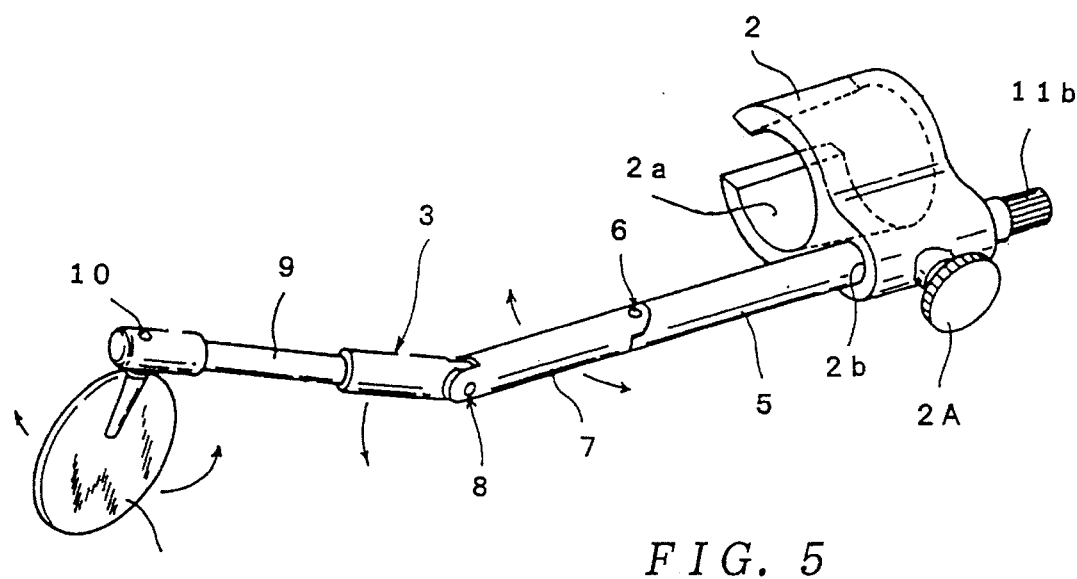
Figure 5:
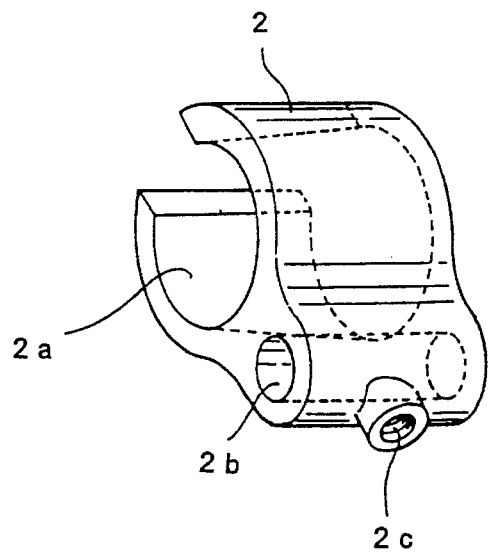

The drilling machine 1, equipped with this displacement equipment, is a common drilling machine for medical treatment with a holding unit at the base 1a. The drilling machine 1 for dentistry is a medical treatment tool formed by the part 1b, which rotates at high speed, driven by compressed or motor, and the drilling tool (bur) 1c, attached to the rolling body 1b.

The displacement equipment of the execution example 1 is shown in FIGS. 1 through 5. This displacement equipment is formed by the installation member 2, which has the C-shaped installation hole 2a that permits the insertion (removable in the axial direction) until the base 1a of the dentistry drilling machine 1, by the arm 3, installed in the supporting hole 2b of the member and by the displacement plate 4, installed on the tip of the arm 3. The arm 3 is formed by the arm 5, supported by the bolt 2A, screwed from the screw hole 2c to the supporting hole 2b of the installation member 2 with sliding mobility, by the medium arm 7, installed through the horizontal rotating mechanism on the tip of the supporting arm 5, and by the tip arm 9, installed through the vertical rotating mechanism on the tip of the medium arm 7.

Horizontal Rotating Mechanism and the Adjustment Mechanism

Since the medium arm 7 mentioned above rotates in the horizontal direction with respect to the supporting arm 5 during utilization of the dentistry drilling machine 1, an adjustment mechanism is necessary to fix the angle of the medium arm 7 with respect to the supporting arm 5, when the oral cavity organs are held being held by means of the displacement plate 4, installed on the tip of the tip arm 9.

Figure 6:
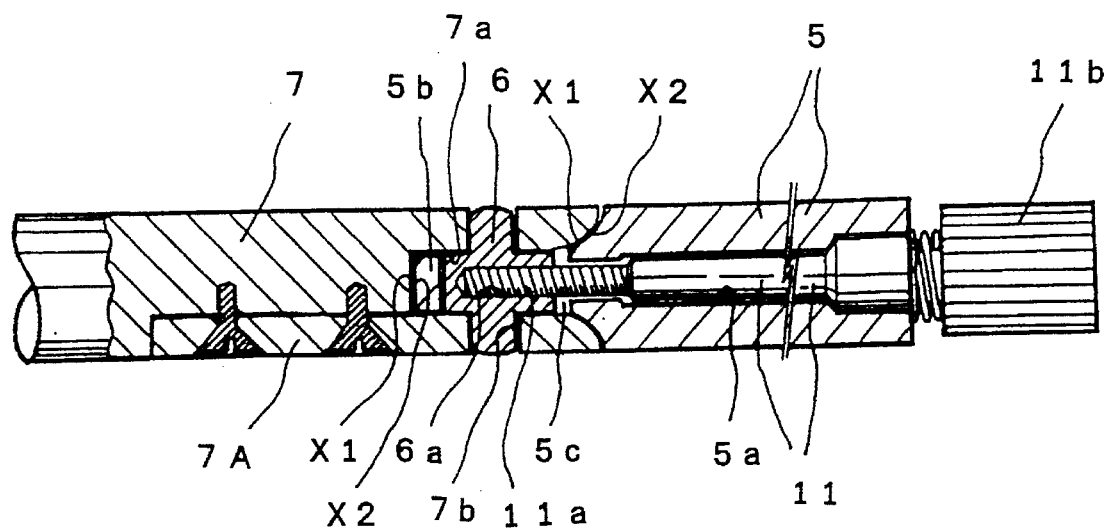
FIGS. 6 to 22 are the sketches showing the rotating mechanism of each member and the corresponding adjustment.
Figure 7:
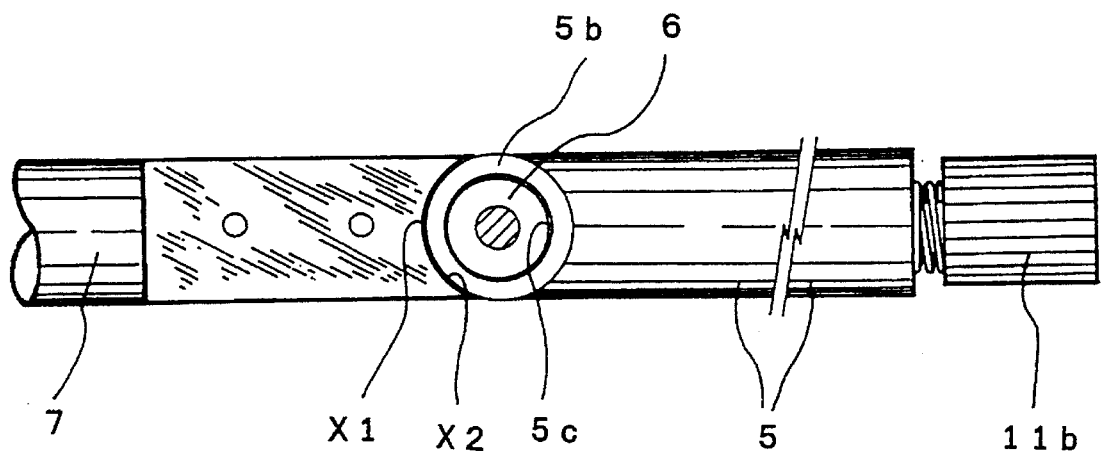

FIGS. 6 and 7 show execution examples of the first rotating mechanism. According to the figure, the concave groove 7a is placed between the medium arm 7 and the partial member 7A, which forms the friction contact surface X1 at the back end of the medium arm 7. The protrusion 5b is placed at friction contact surface X2 on the tip of the supporting arm 5, against the friction contact surface X1.

FIG. 6 shows the split member 7A, extracted from the medium arm 7. From this figure, it can be easily seen that friction contact surfaces X1 and X2 form an arc, and that the horizontal rotating movement of the supporting arm 5 and the medium arm 7 is possible thanks to the connection with the rotating axis 6. The friction contact surfaces X1 and X2 are also formed at the interface between the back end of the medium arm 7 and the supporting arm 5.

The rotating axis 6, mentioned above, besides having axial centers on both sides, have screws 6a at the center of the body, with diameter slightly bigger than that of the axis center. The bearing hole 5c is constructed to be attached to the body of the rotating axis 6, in the before-mentioned protrusion 5b of the supporting arm 5. The bearing hole 7b is constructed to fit the rotating axis 6 mentioned above, on both walls of the concave groove 7a, which is located at the back end of the medium arm 7.

According to the figure, the before-mentioned supporting arm 5 is formed by a pipe-shaped member with the hollow axis 5a. Inside the hollow axis 5a, on the tip there are screw 6a and thread section 11a in the body of the already mentioned rotating axis 6, and the operation rod 11 with the operation member 11b, which makes supporting arm 5 rotate around the axis, at the back end.

When the dentist who is using the protective equipment of this invention causes the operation member 11b of the already mentioned operation rod 11 to rotate, the tip of operation rod 11 pulls the body of the rotating axis 6 towards the supporting arm 5 due to the connecting screws, because the wall of the operation member 11b and the back-end wall of the supporting arm 5 are in contact.

On the other hand, since the rotating axis 6 is inserted into the bearing hole 7b, constructed at the back end of the already mentioned medium arm 7, the friction resistance of the friction contact surfaces X1 and X2 increases, and the supporting arm 5 and the medium arm 7 are set into a fixed angle.

Figure 8:
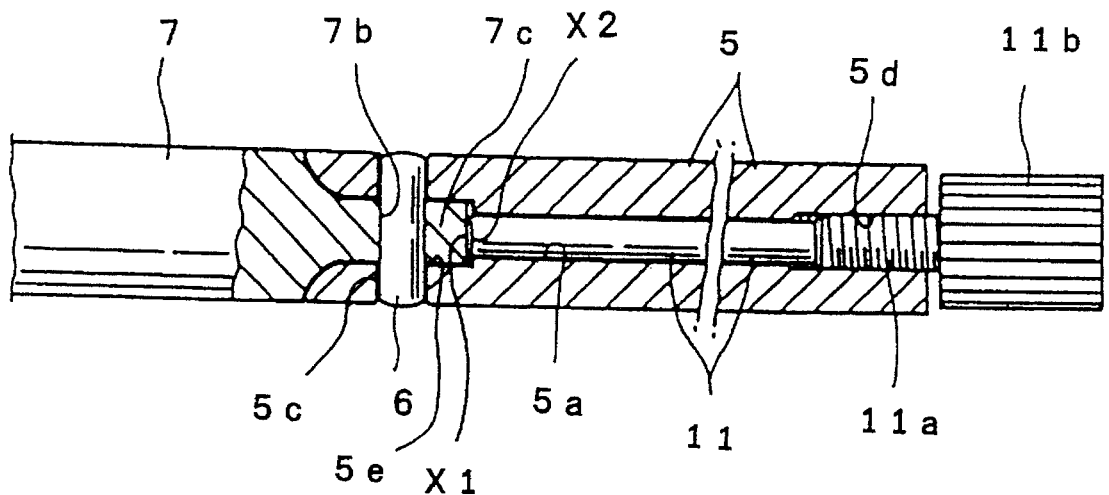
Figure 9:
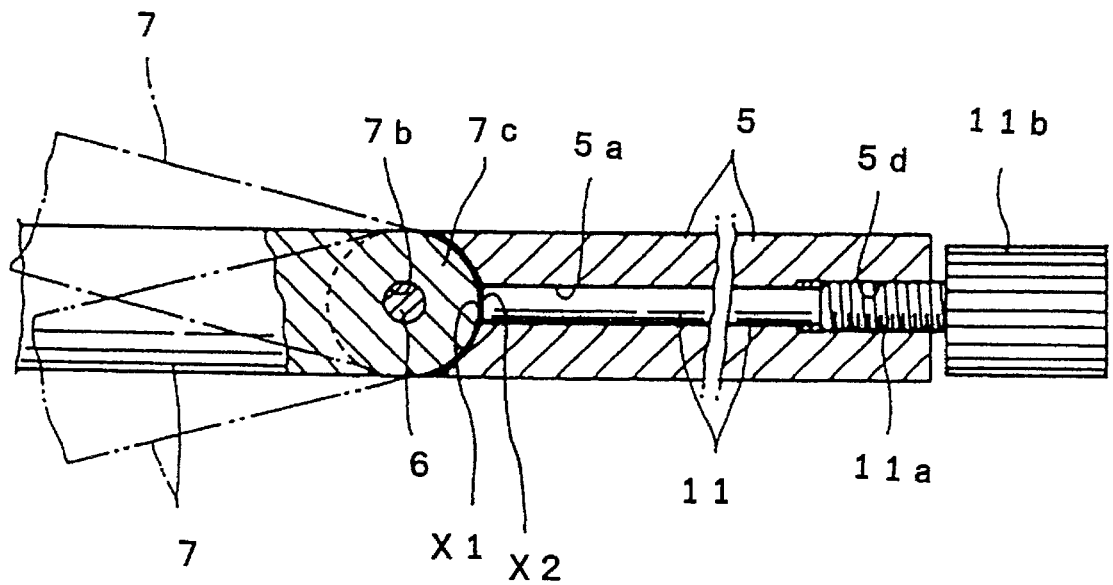

FIGS. 8 and 9 show the second execution example of the rotating mechanism. In this case, the protrusion 7c is constructed at the back end of the medium arm 7, the and friction contact surface X1 is placed at the protruding part 7c. The concave groove 5e is placed on the tip of the supporting arm 5 and inserted into the rotating axis 10, into the protruding part 7c and into the bearing hole 7b, constructed at both walls of the concave groove 10.

There is friction between surface X1 and surface X2, built at the end surface of the operation rod 11. The operation rod 11 is constructed in the hollow axis 5a with advance-and-retreat mobility, due to the connection of thread part 11a, installed in the back end of the outer surface, and the thread part 5d, installed in the inner surface of the back end of the supporting arm 5.

Figure 10:
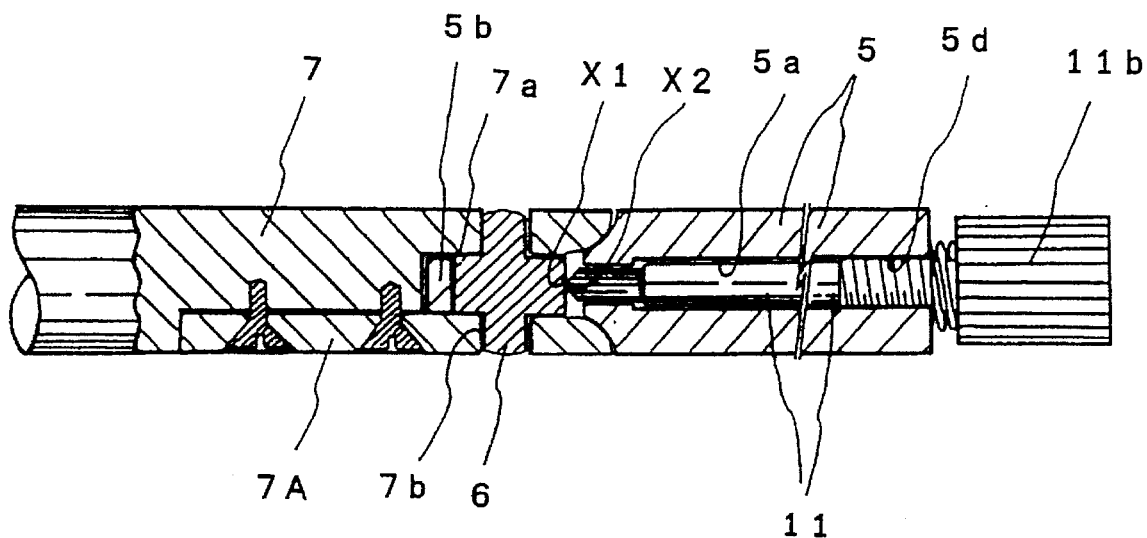
Figure 11:
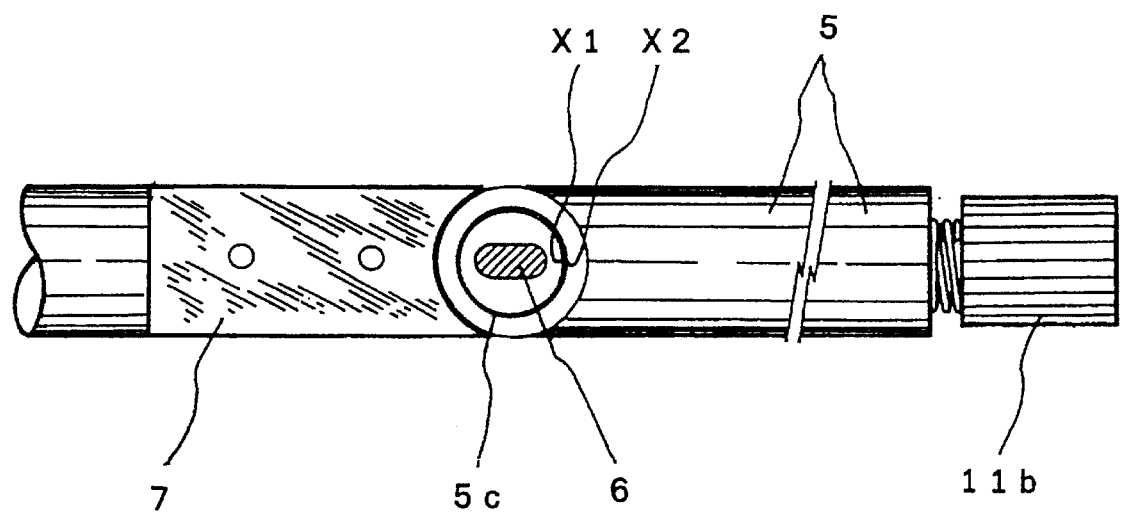

FIGS. 10 and 11 show execution examples of the rotating mechanism number 3. In this execution example, the surface X1 of the medium arm 7 is placed in the body of the rotating axis 6. For that reason, the rotating axis 6 forms a semi-elliptic surface, so that the axial center of the rotating axis 6 does not rotate with respect to the bearing hole 7b of the medium arm 7.

On the surface X1 of the body of the rotating axis 6 mentioned above, a hollow part could be constructed in the ideal case (it is not shown in the figure). Friction may occur with surface X2, built on the tip of the operation rod 11.

Figure 12:
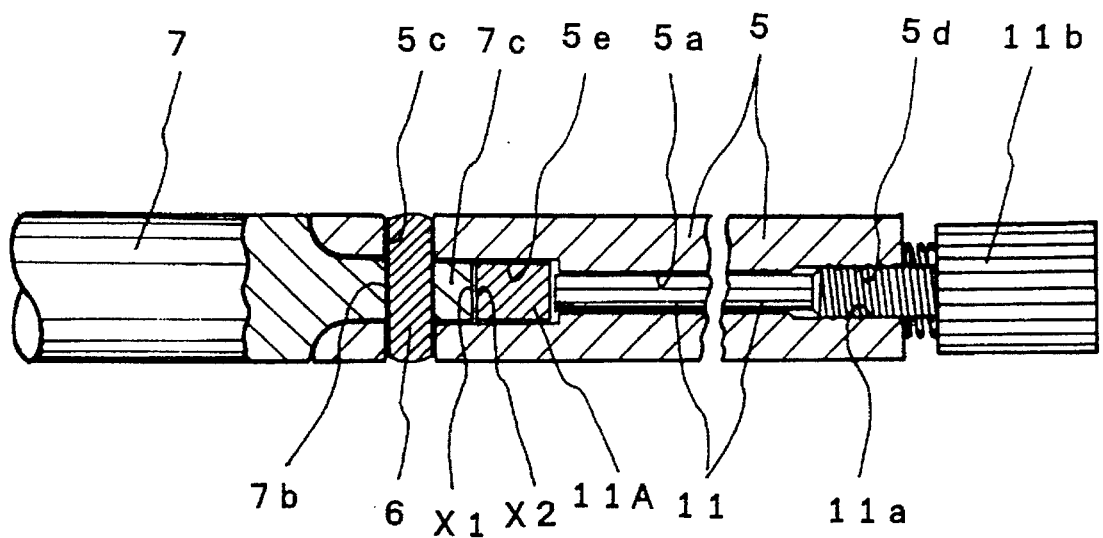
Figure 13:
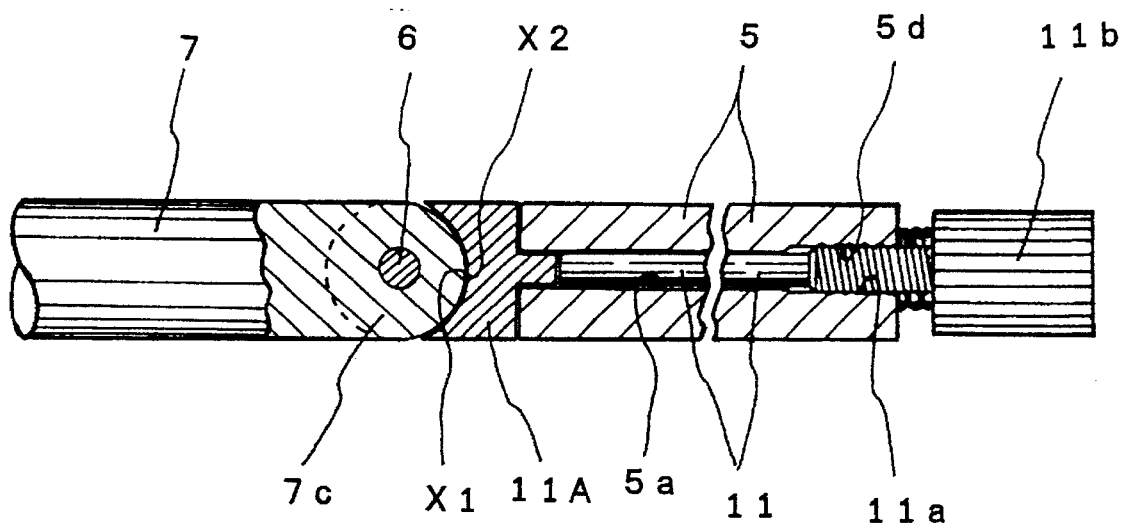

FIGS. 12 and 13 show an execution example of the rotating mechanism 4. In this execution example, there is friction between the surface X1, mounted at the back end of the medium arm 7, and the surface X2 of the operation member 11A, placed on the tip of the operation rod 11. The operation rod 11 pulls the press member 11A towards the tip, through the operation of the operation member 11b. In the case of this execution example, there is no need to use a split member in the medium arm 7.

Rotating Mechanism in the Vertical Direction and Adjustment Mechanism

Figure 14:
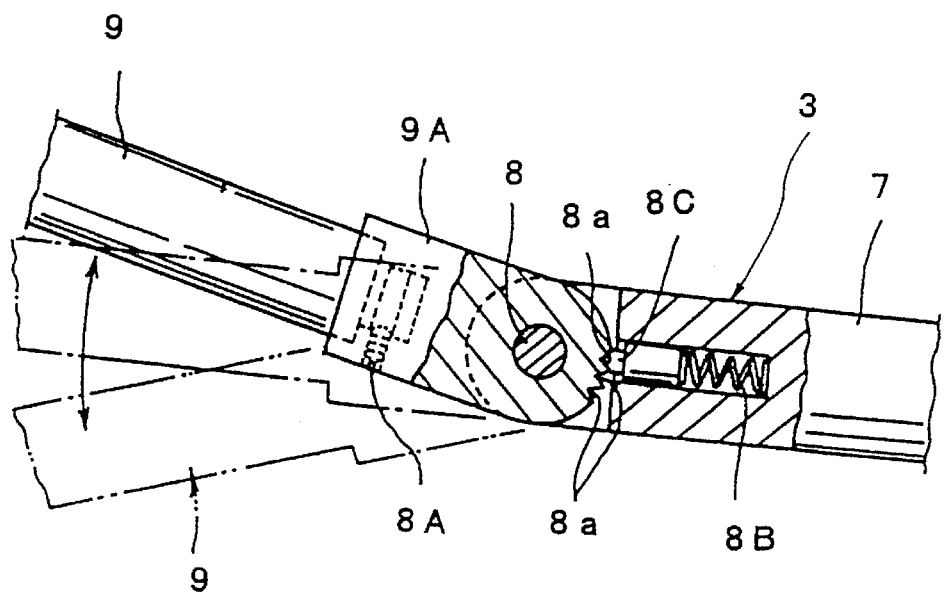
Figure 15:
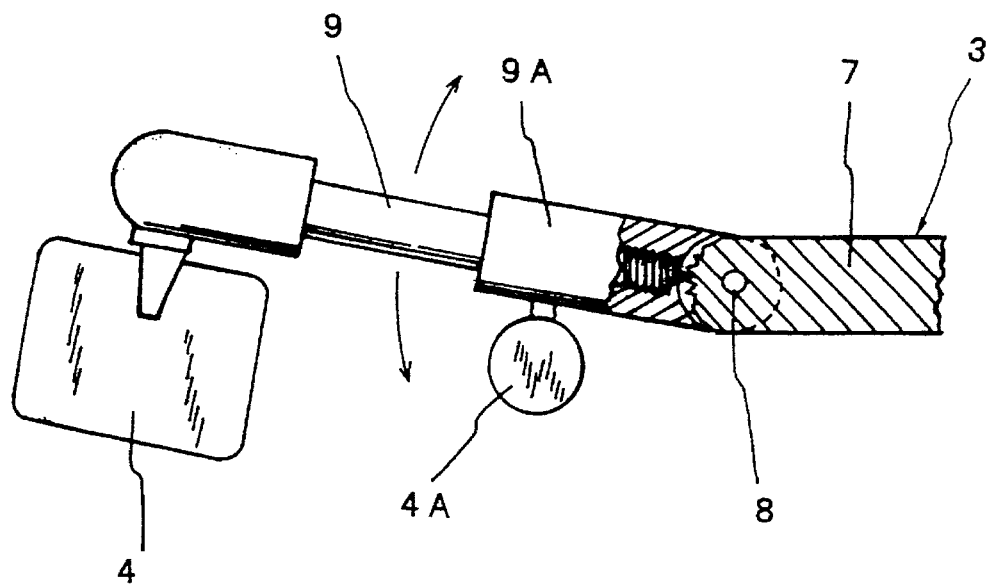

FIGS. 14 and 15 show a slightly different rotating mechanism in the vertical direction. In the rotating mechanism of FIG. 15, the tip arm 9 and the medium arm 7 can be fixed through operation of the member 4A.

Other Adjustment Mechanisms

Figure 16A:
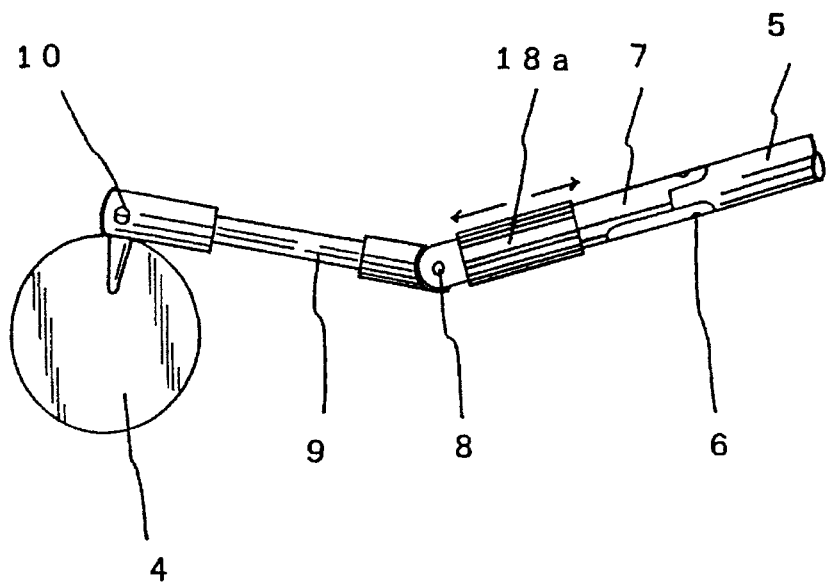
Figure 16B:
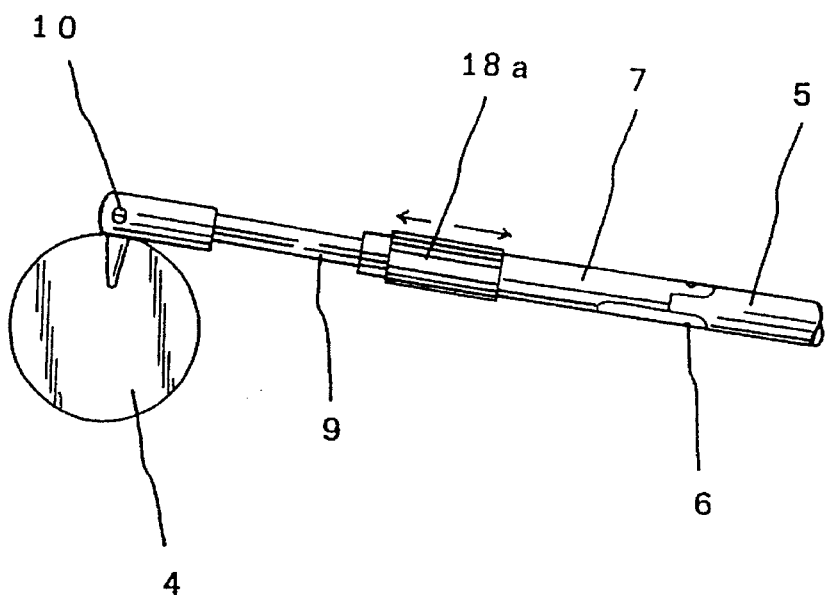
Figure 17A:
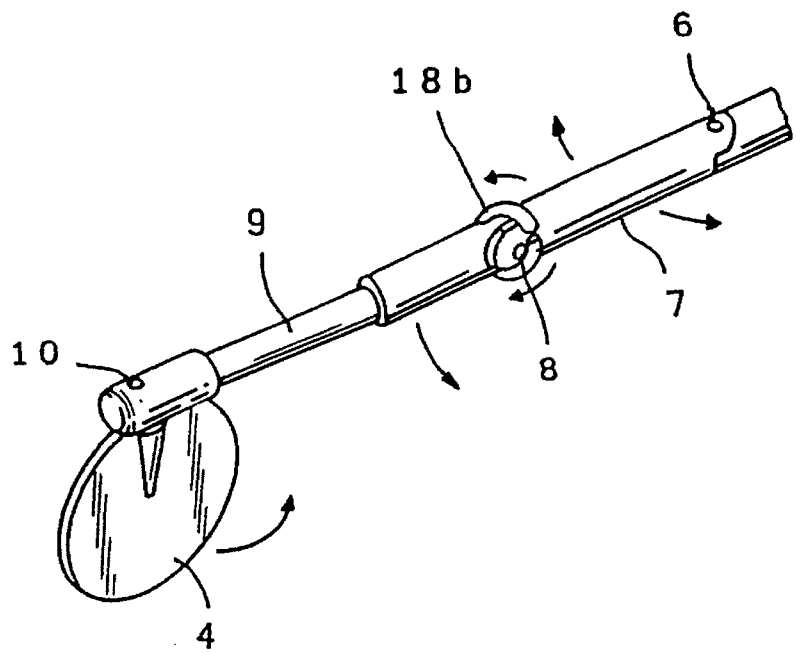
Figure 17B:
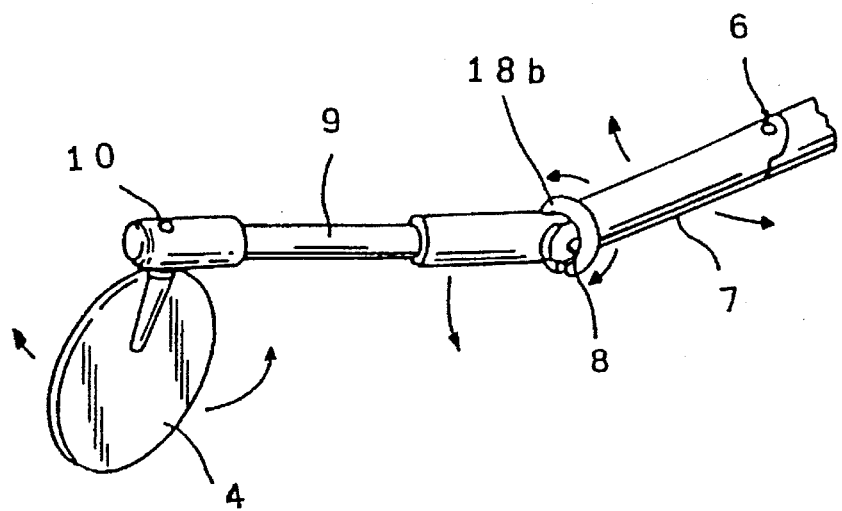
Figure 18:
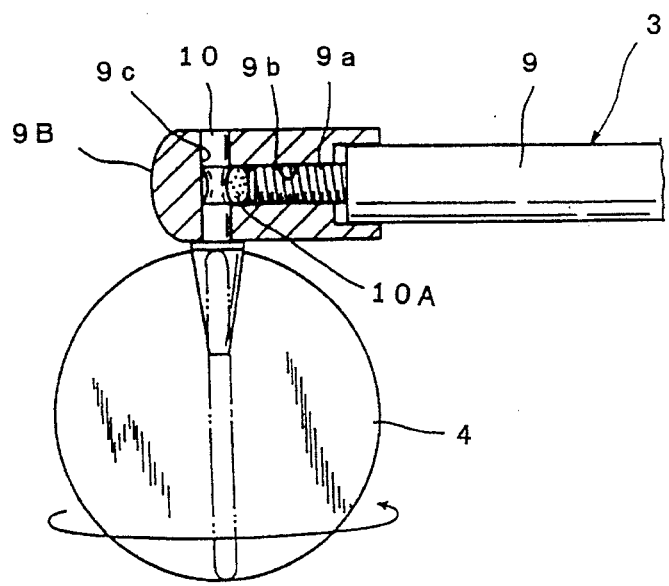
Figure 19:
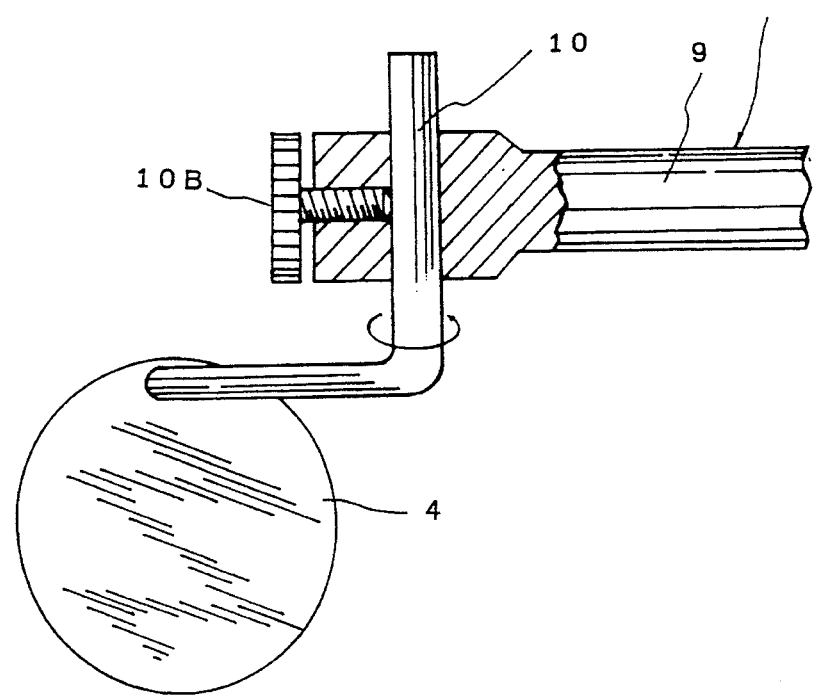
Figure 20:
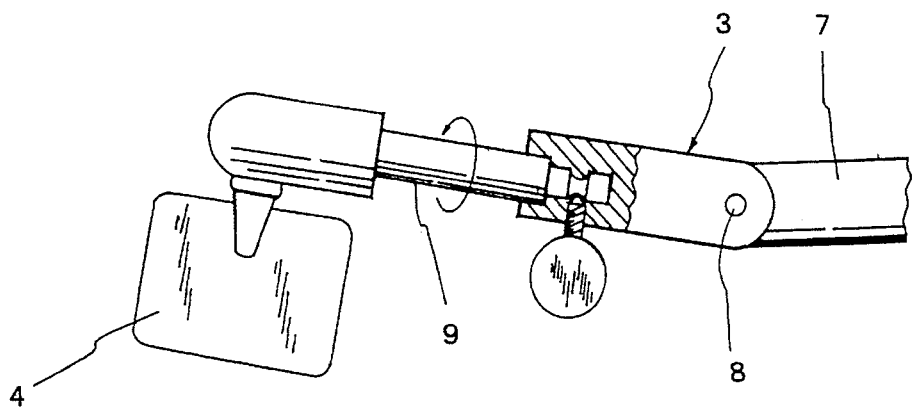
Figure 21:
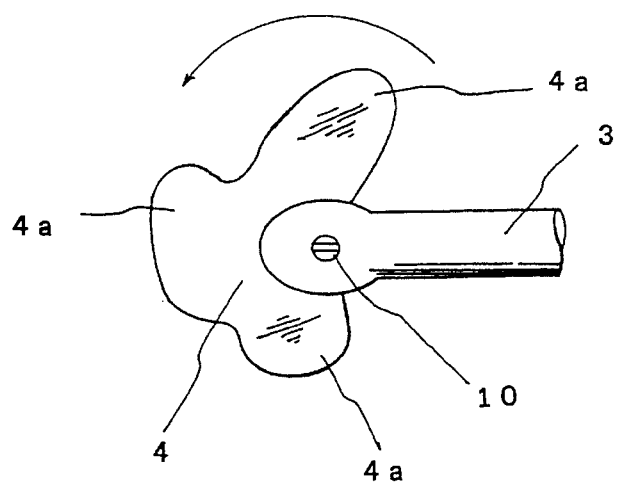
Figure 22:
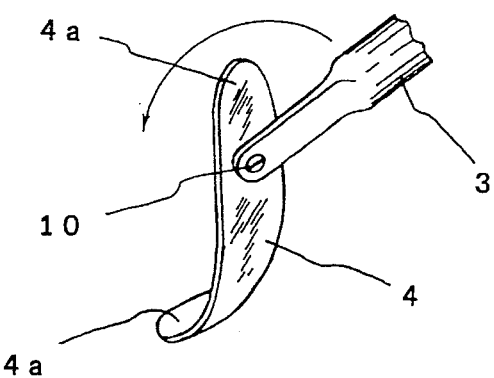
Figure 23:
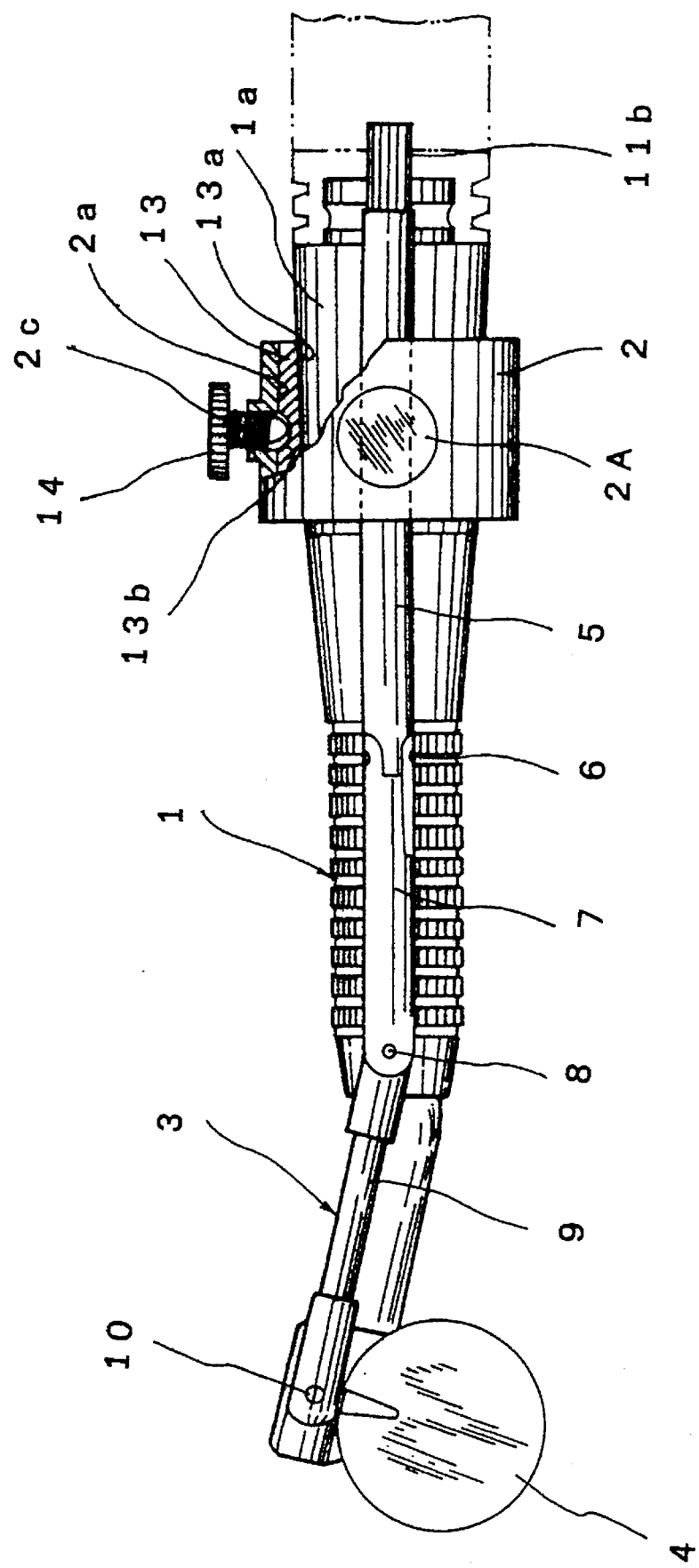
FIGS. 23 to 36 are the sketches showing the displacement equipment of execution examples 2 and 9.
Figure 24:
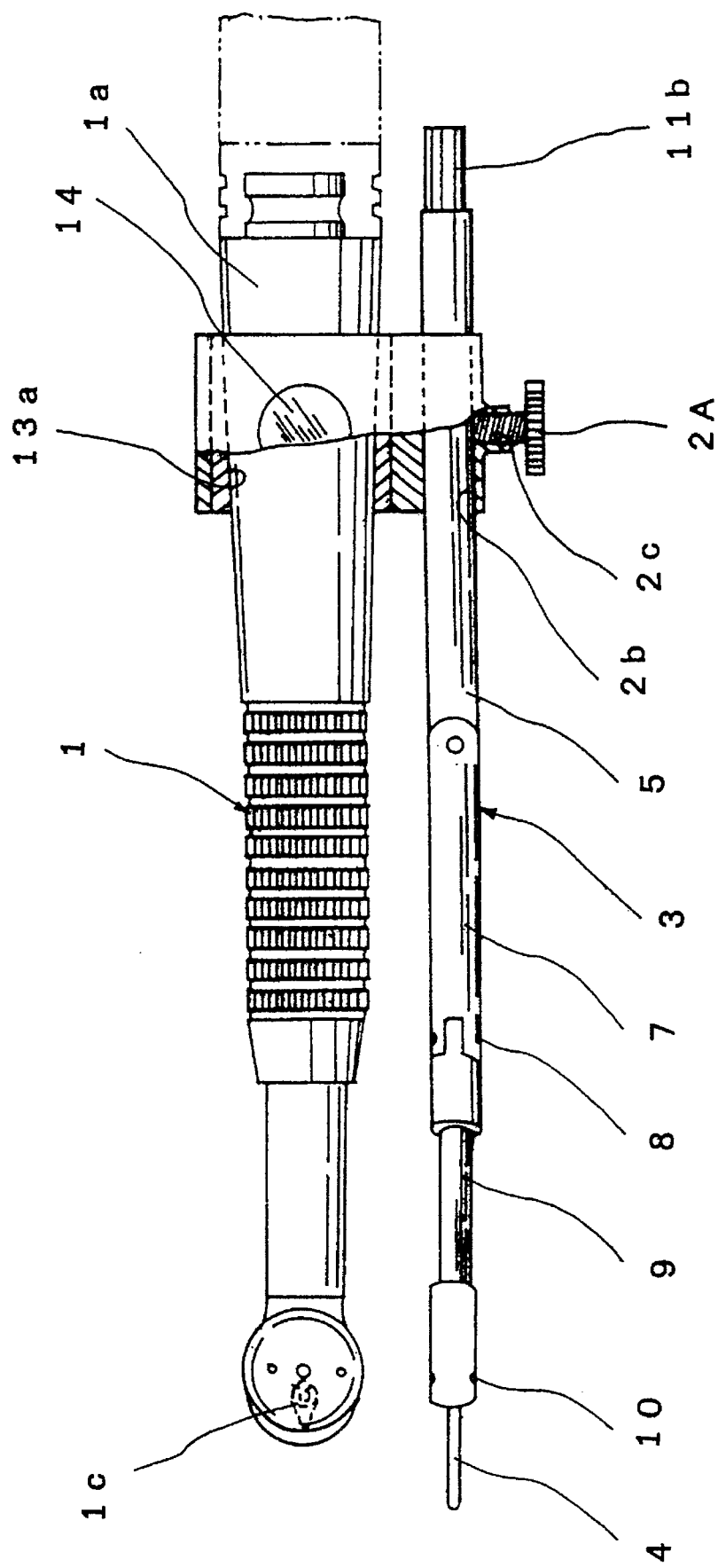
Figures 25, 26:
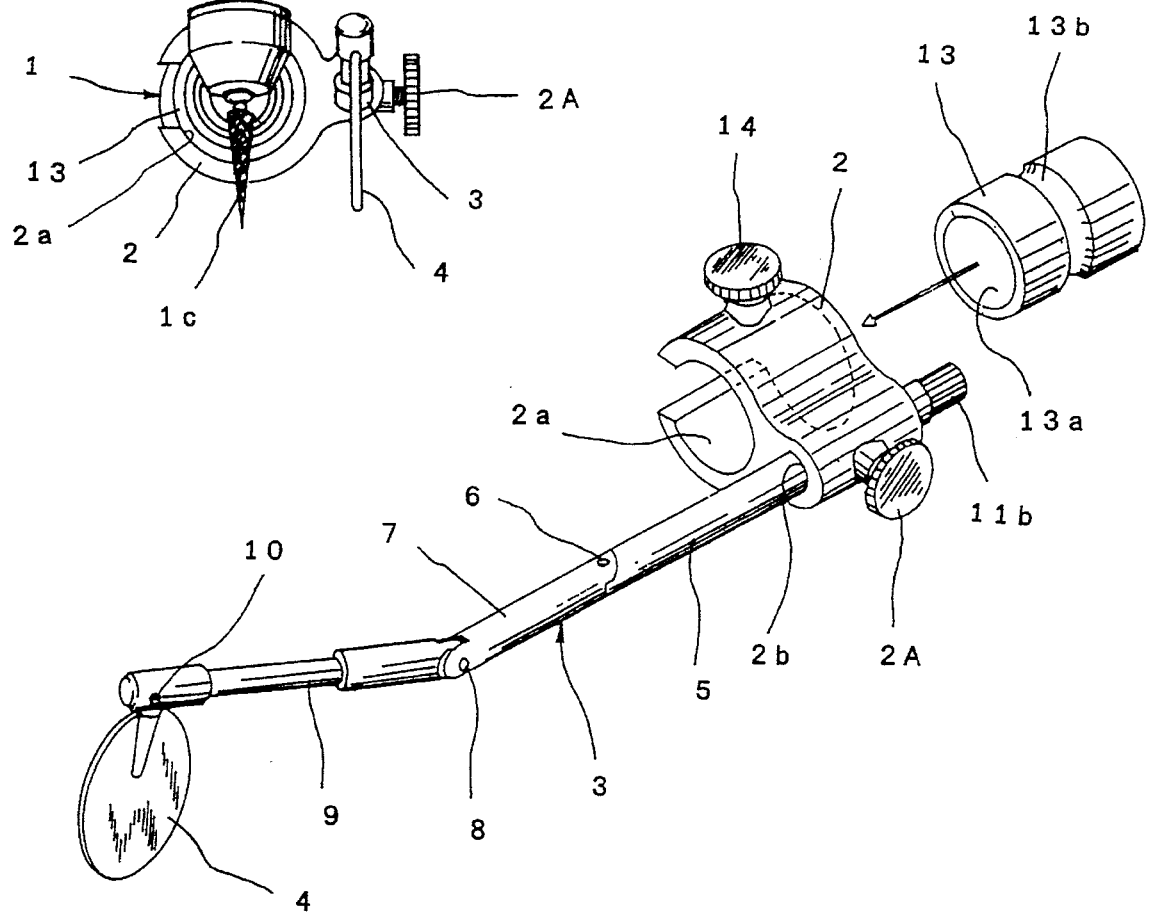

FIGS. 16 and 17 show another execution example of rotating mechanism. This rotating mechanism is installed through the rotating axis 8, between the tip arm 9 and the medium arm 7, which are connected with each other. In this execution example, the adjustment pipe 18a, which can move in the direction of the axis of the medium arm 7, is placed on the outer surface of the medium arm 7 (or the tip arm 9). By moving the adjustment pipe 18a towards the rotating axis 8, it is possible to fix the tip arm 9 and the medium arm 7 along a straight line.

Rotating Mechanism of the Displacement Plate and the Displacement Plate

The displacement plate 4, as shown in FIGS. 18 through 22, are installed on the tip of the arm 3, through a rotating mechanism. In the displacement plate 4, seen in the FIGS. 21 and 22, two or more differently-shaped tongue-shapes (number 4a) are constructed on the outer direction, around the rotating axis. The construction permits the tongue shape 4a to be selectively utilized according to the shape of the oral cavity, by rotating the displacement plate 4. In the displacement plate of execution example 2, as shown in FIGS. 23 through 26, the inner tube 13 is installed between the base part 1a and the installation member 2 of the dentistry drilling machine 1. The inner tube 13 has for example the tapered installation hole 13a, fixed to base part 1a of the dentistry drilling machine 1. Furthermore, the outer surface of the inner tube 13 and the inner surface of the installation hole 2a of the installation member 2 are coaxial cylinders.

The U-shaped channel 13b is constructed in the form of a ring on the outer surface of inner tube 13, mentioned above, and the ring-shaped head part of bolt 14, screwed into the screw hole 2c from the outside of the previously mentioned installation member 2, is projected into the U-shaped ring 13b of the inner tube 13. The dentistry drilling machine 1 is constructed so that it cannot move in the axial direction, with respect to the installation member 2. By fastening the bolt 14 tight, it is possible to keep the dentistry drilling machine 1 from rotating, but the axial rotation of dentistry drilling machine i with respect to installation member 2, during utilization, is possible.

Figure 27:
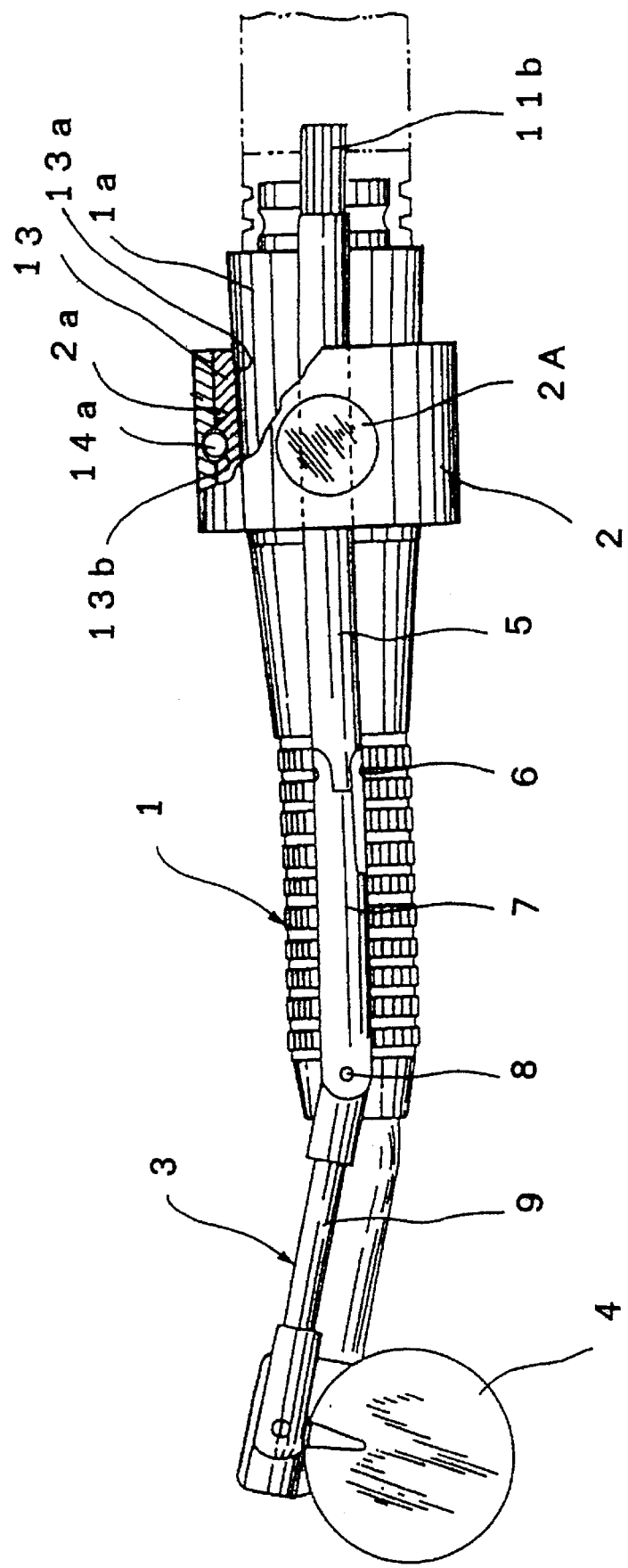
Figure 28:
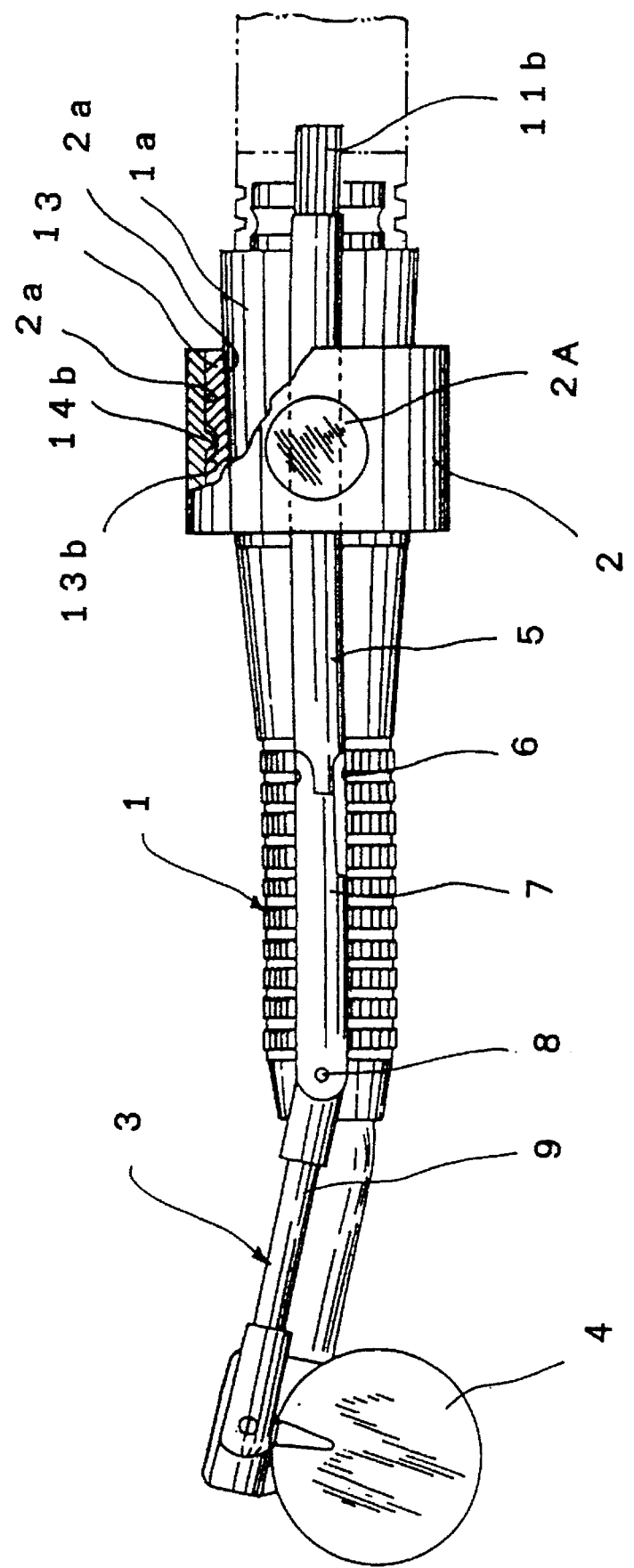

In the displacement equipment of the execution example 3, as shown in FIG. 27, the ball bearing 14a is constructed between the U-shaped channel of the installation member 2 and the U-shaped channel 13b of the inner tube 13. In the displacement equipment of the execution example 4, as shown in FIG. 28, the ring-shaped protrusion 14b, which is projected into the U-shaped channel 13b, is constructed on the inner surface of installation member 2.

Figure 29:
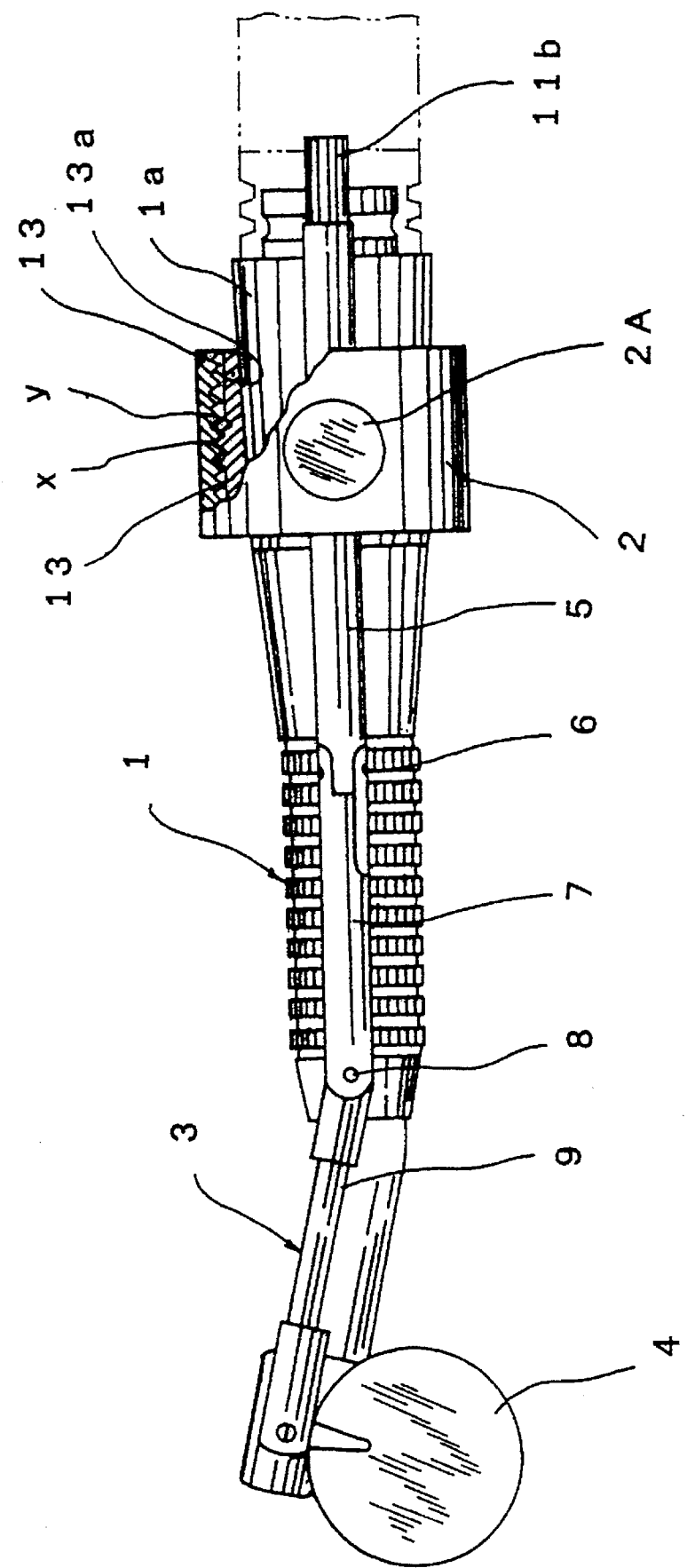
Figure 30:
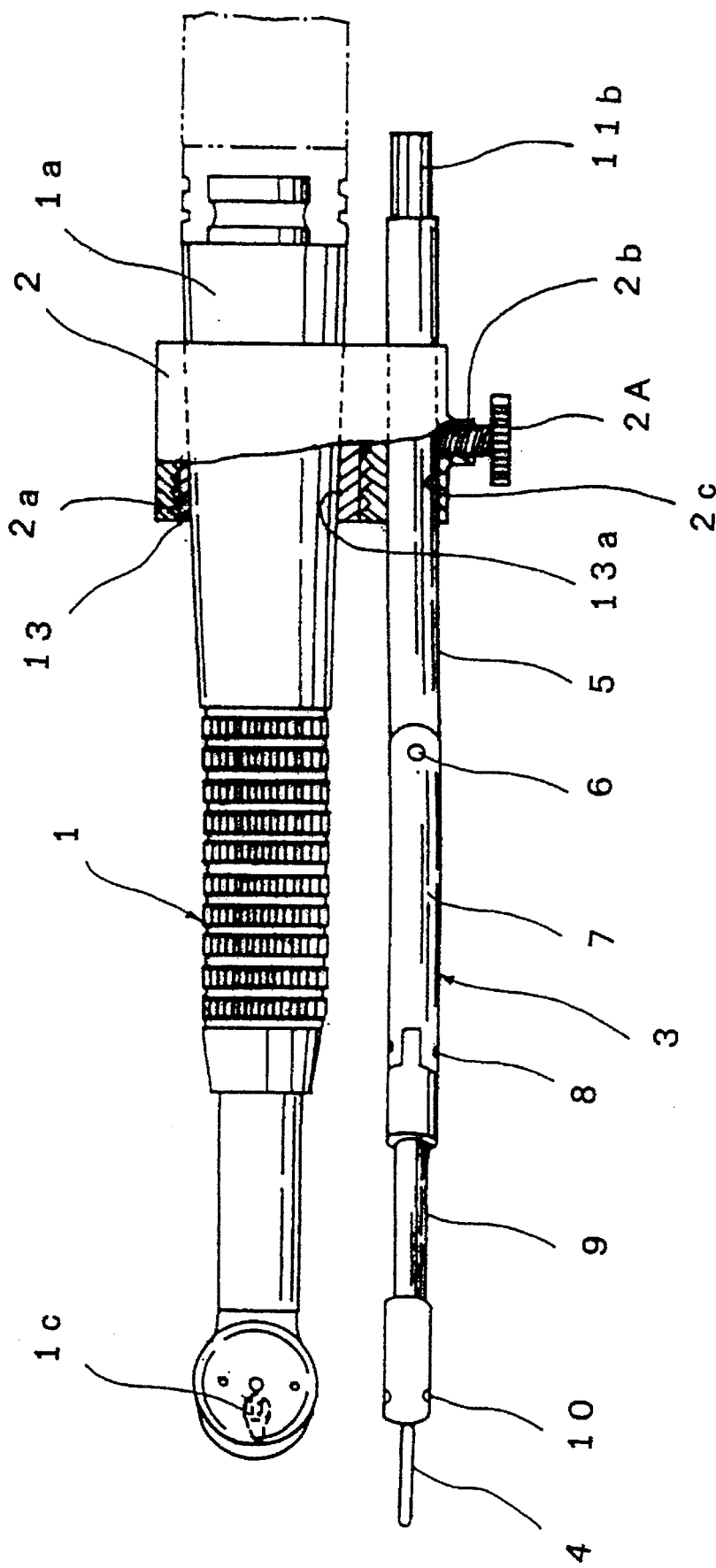

In the displacement equipment of the execution example 5, as shown in FIGS. 29 and 30, the inner tube 13, similar to that used in the execution example 4, is installed between the base part 1a and the installation member 2 of the dentistry drilling machine 1. The thread part y is constructed in connection with the thread part x, built in the inner surface of the installation hole 2a of the installation member 2, on the outer surface of the inner tube 13. During the rotation of the dentistry drilling machine 1, it does advance-and-retreat movement with respect to the installation member 2.

Figure 31:
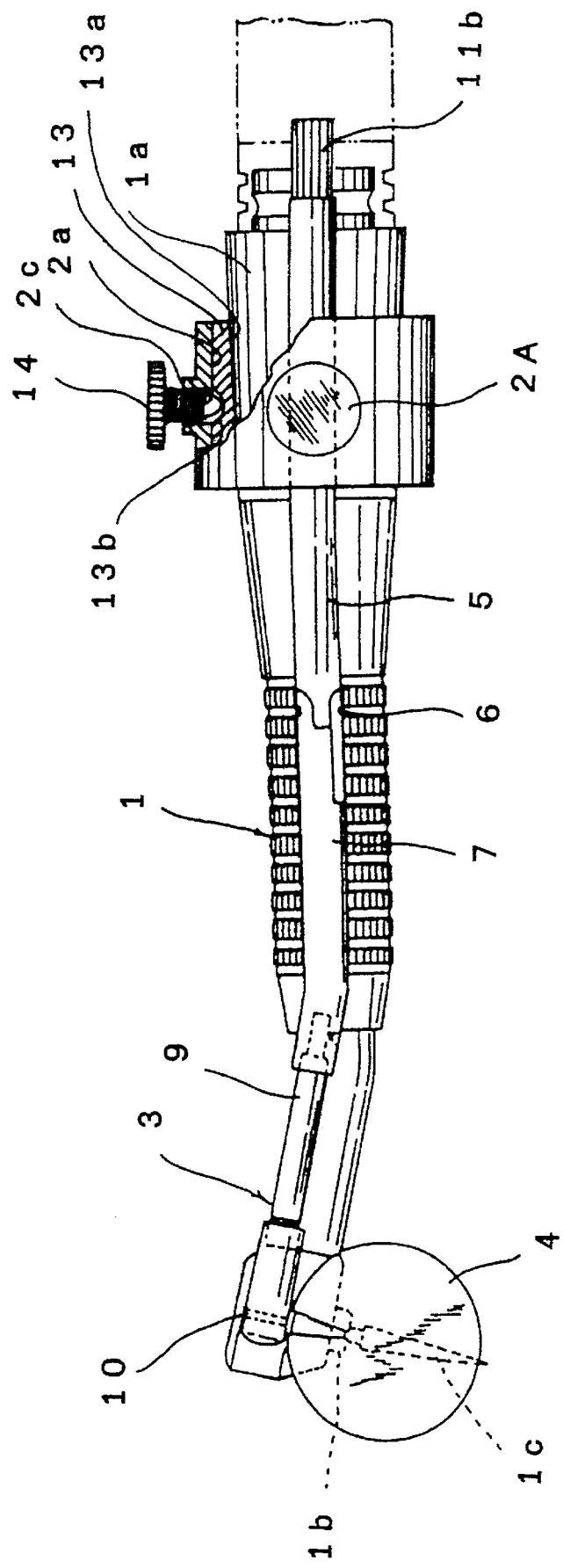

In the displacement equipment of execution example 6, as shown in FIG. 31, the rotating mechanism in the vertical direction is omitted.

Figure 32:
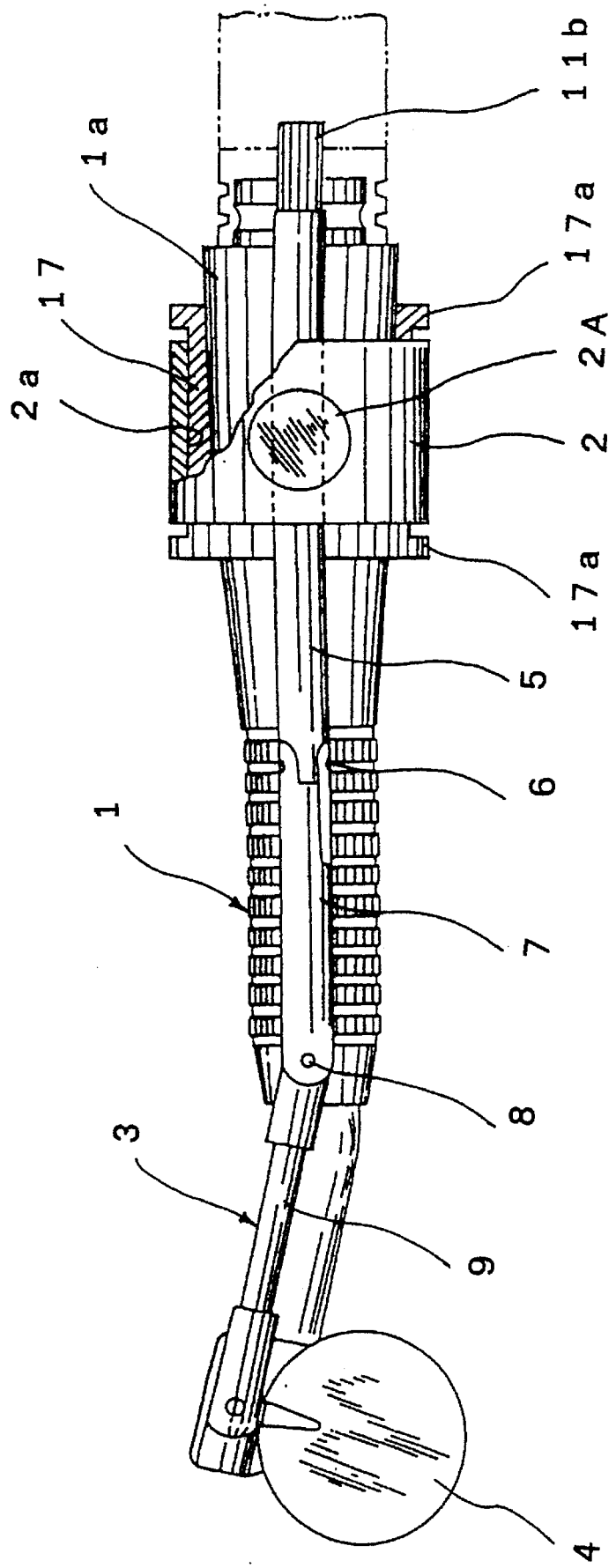
Figure 33:
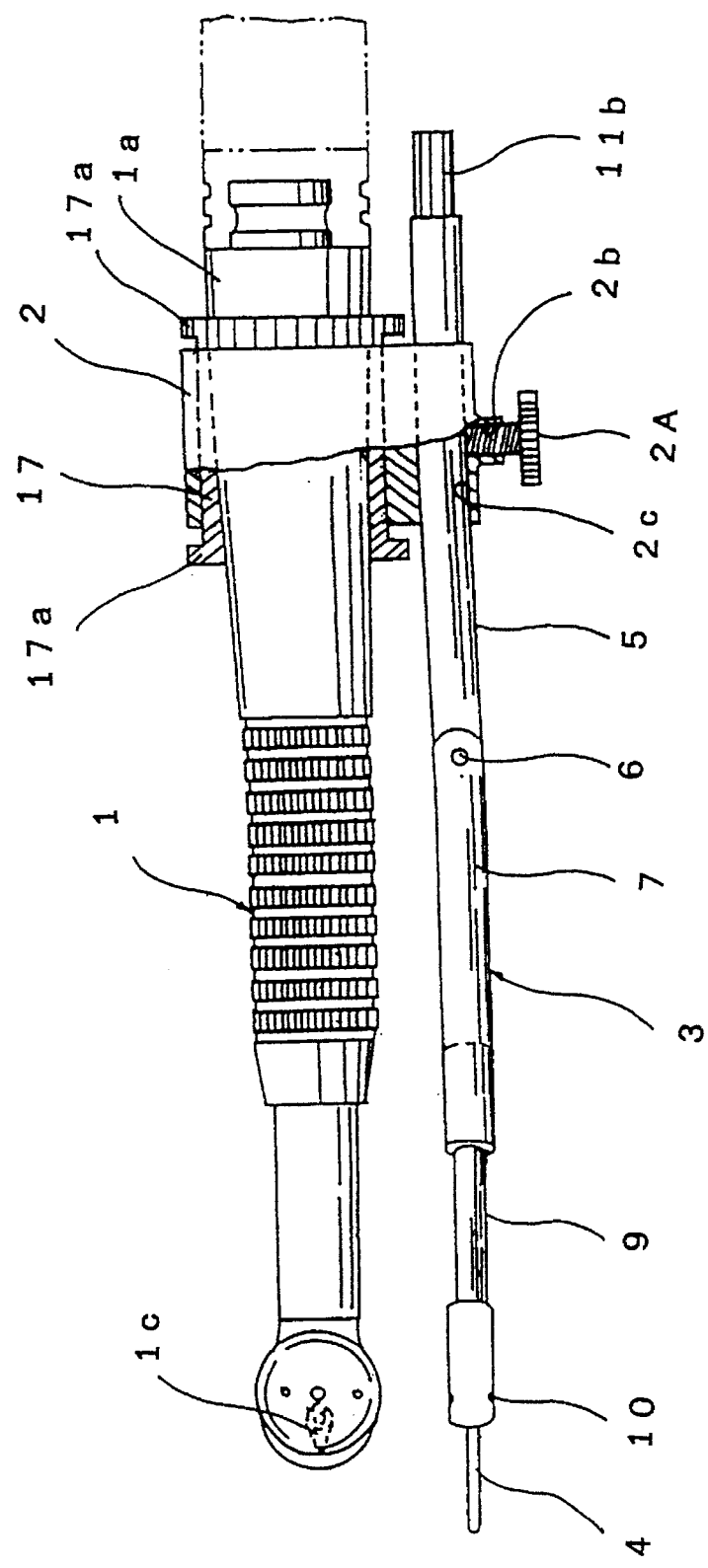
Figure 34:
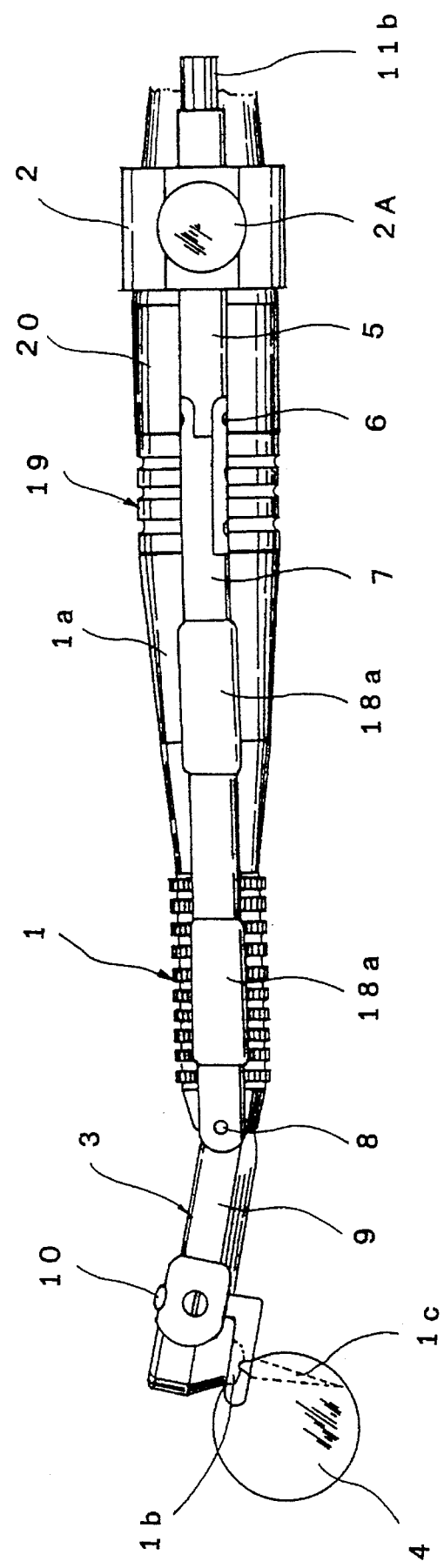
Figure 35:
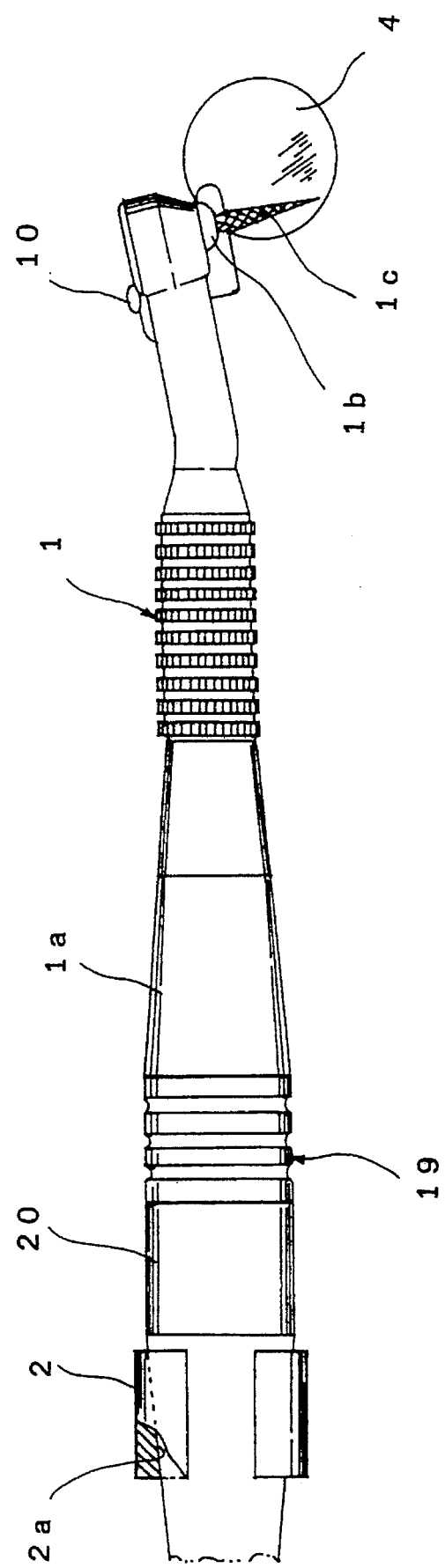
Figure 36:
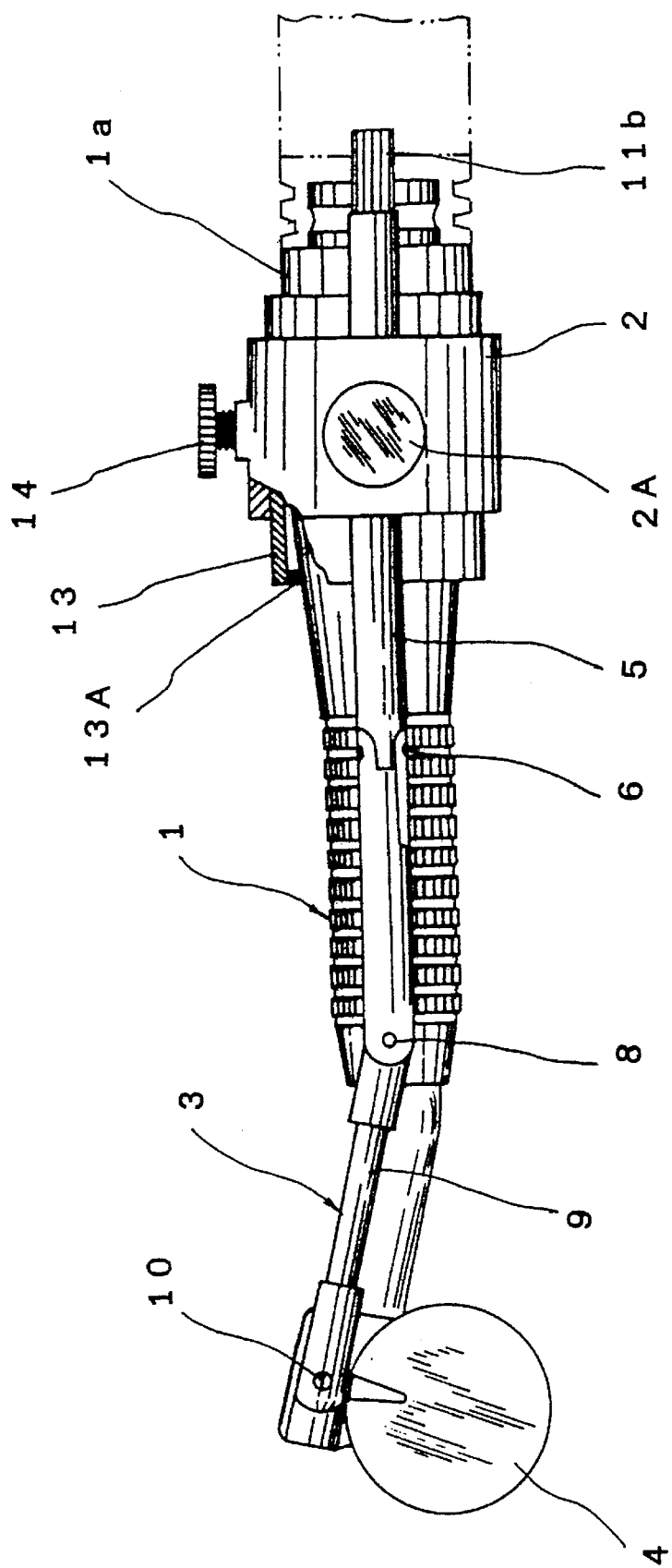
Figure 37:
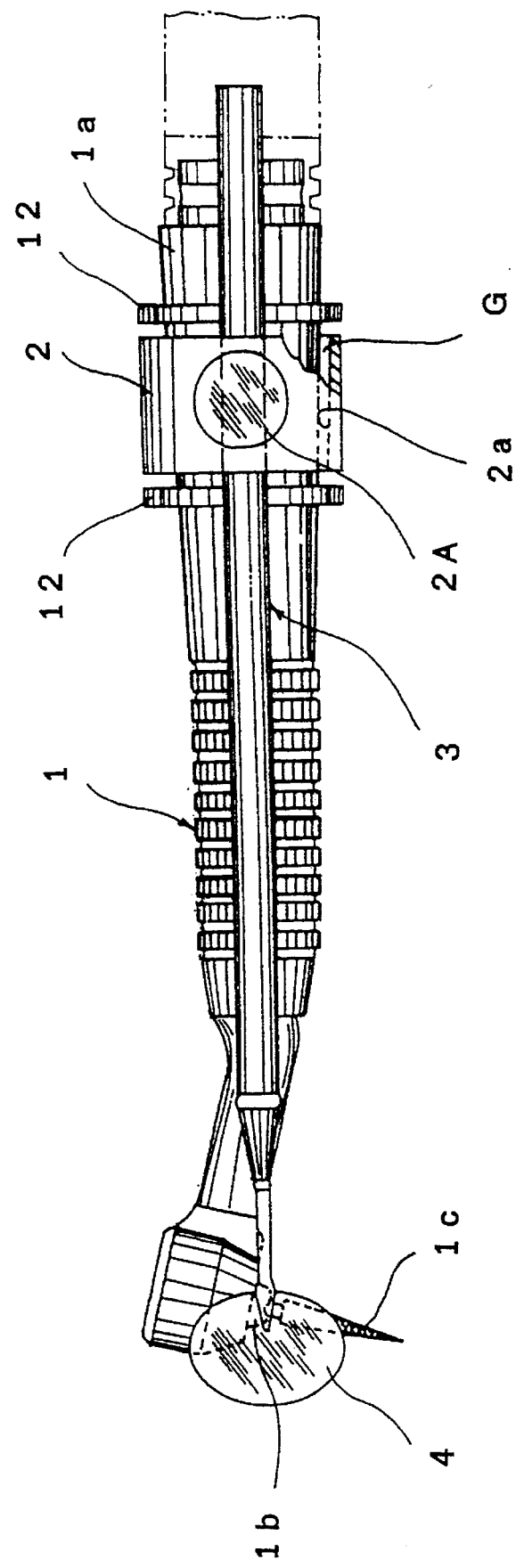
FIGS. 37 to 50 are the sketches of the displacement equipment of execution examples 10 and 13.
Figure 38:
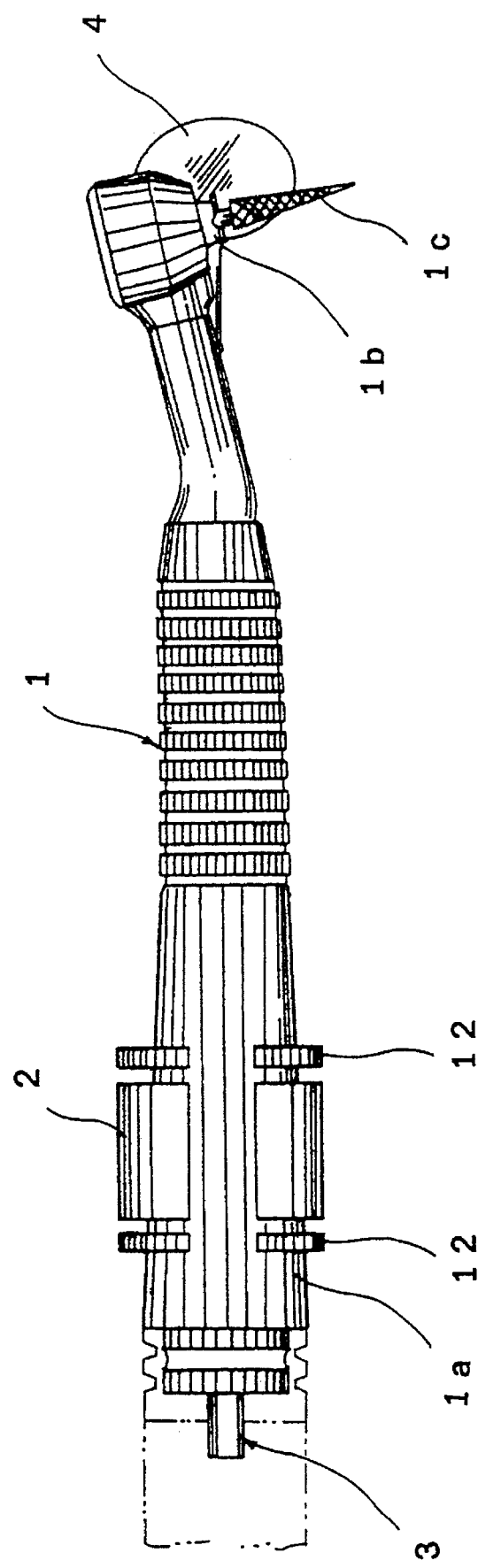
Figure 39:
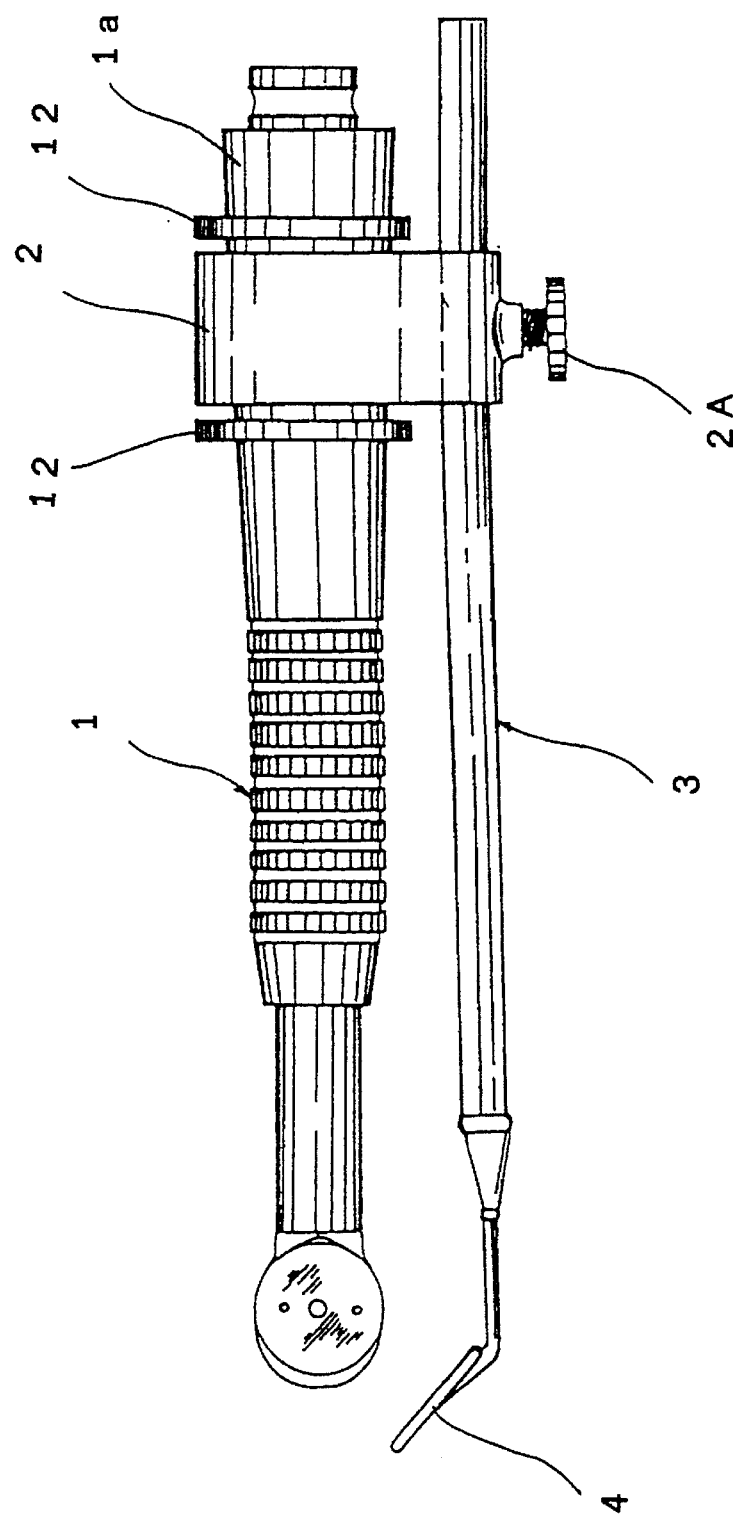
Figure 40:
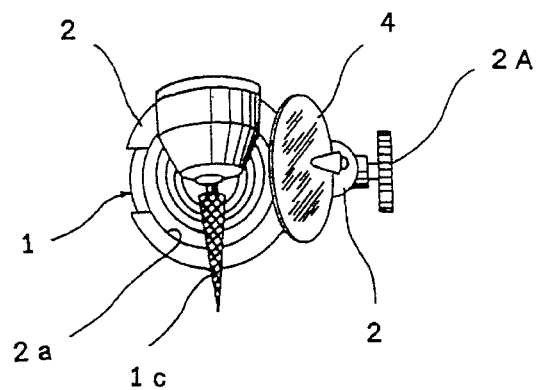
Figure 41:
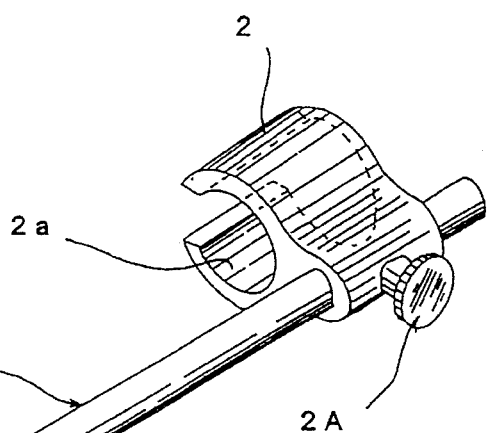
Figure 42:
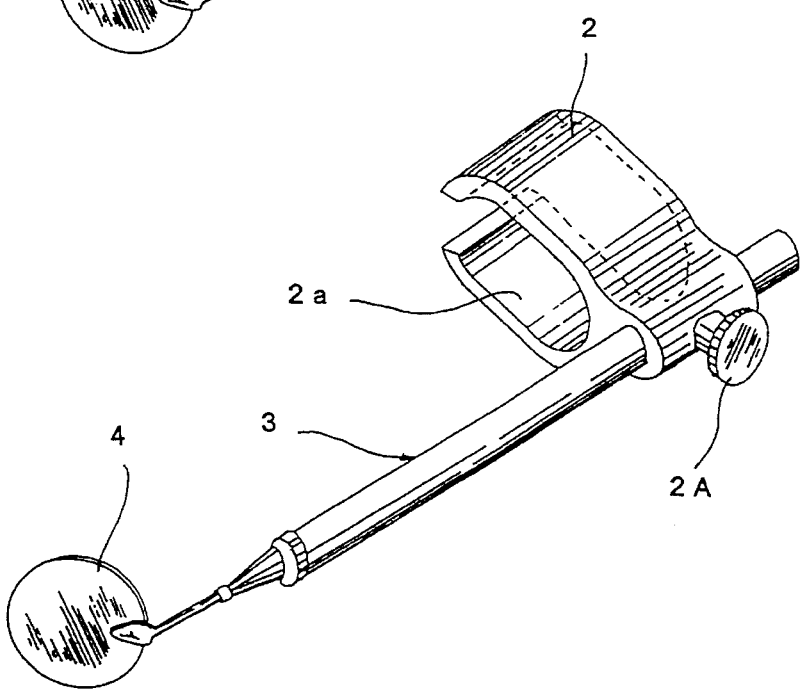
Figure 43:
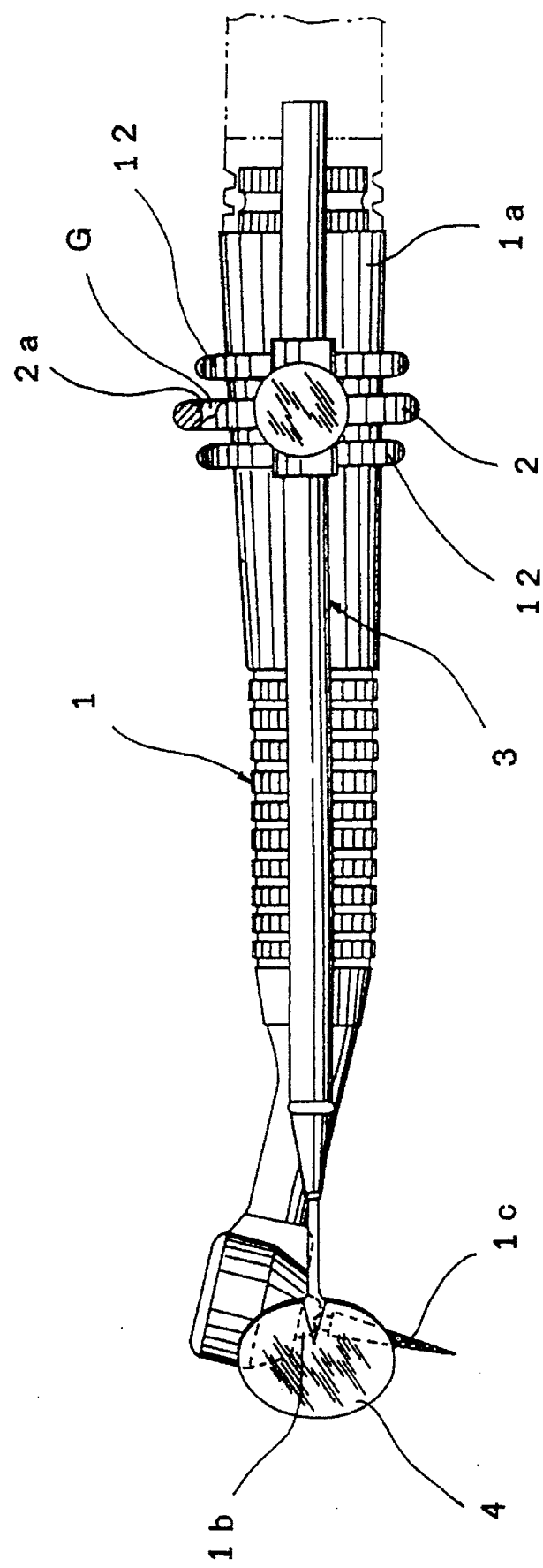
Figure 44:
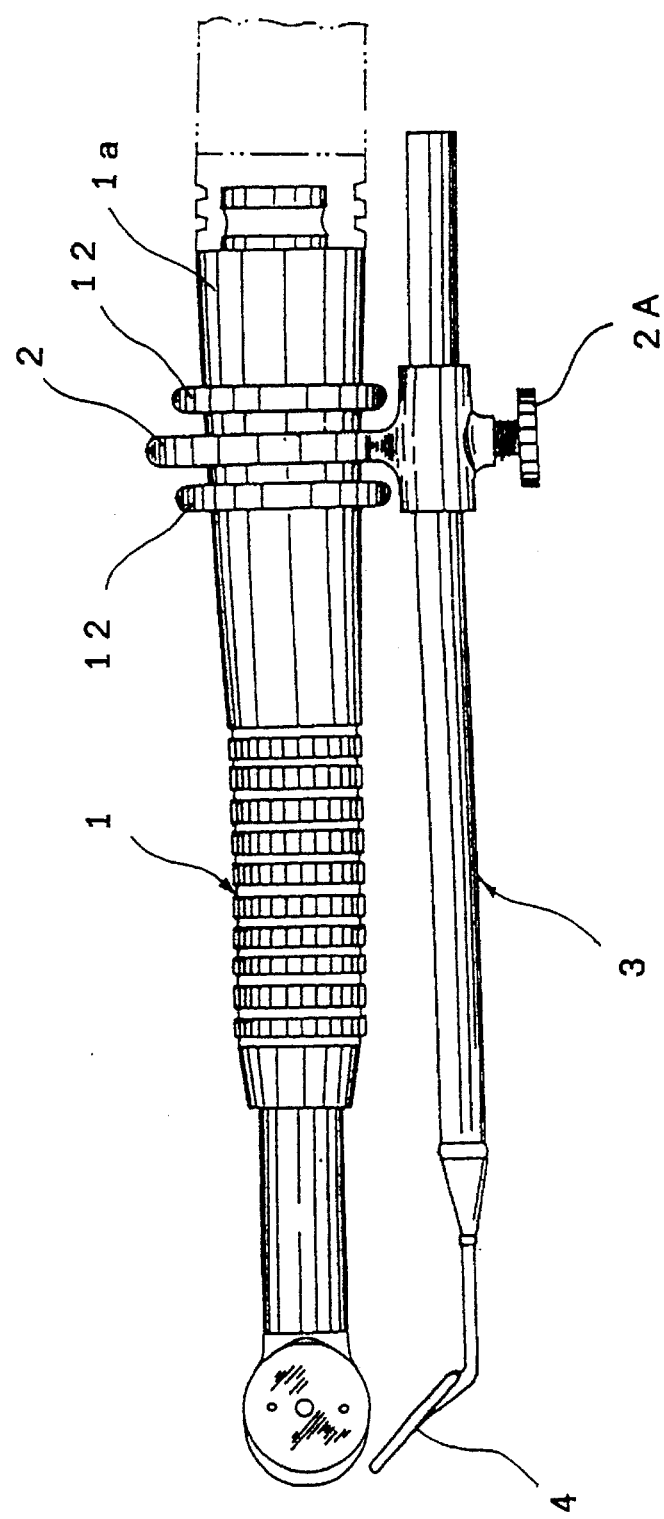
Figure 45:
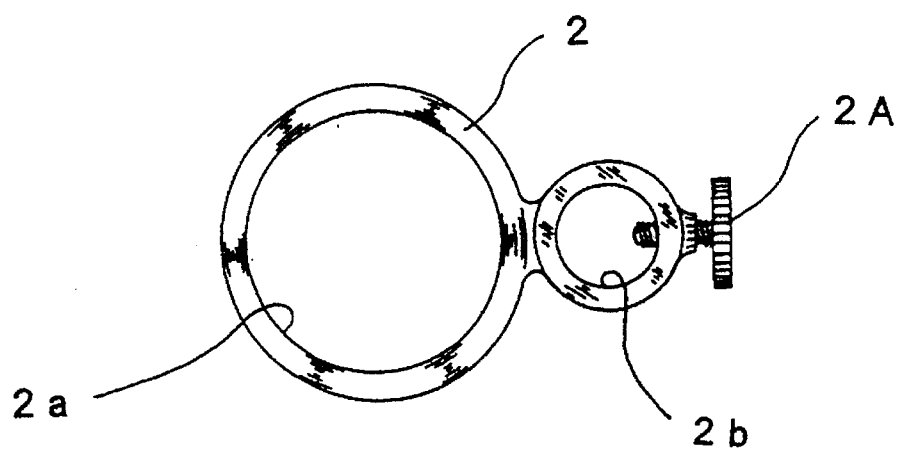
Figure 46:
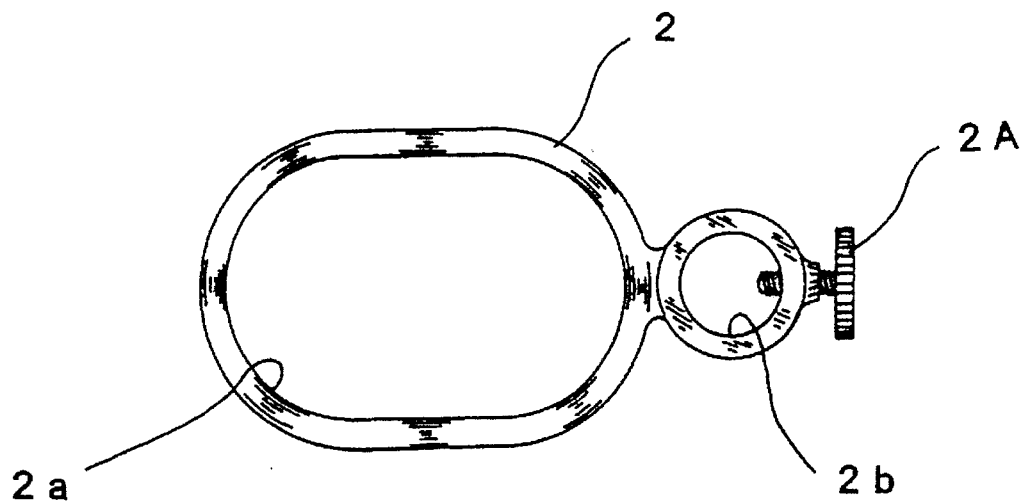
Figure 47:
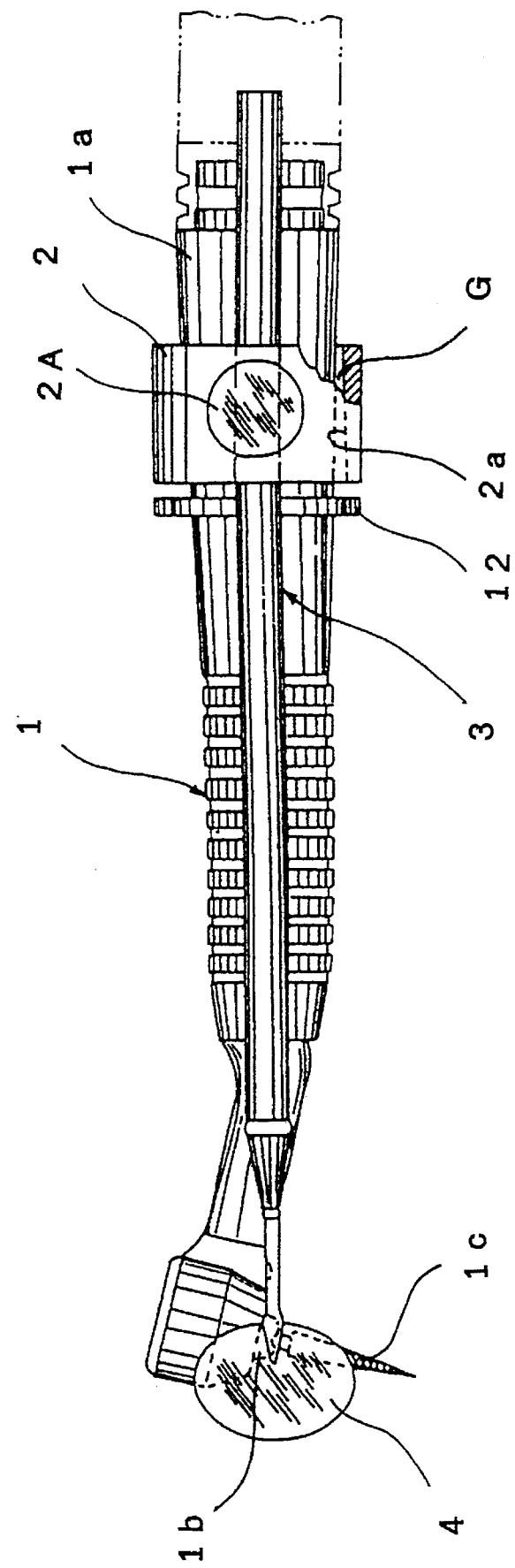

FIGS. 32 and 33 show execution example 7. In this displacement equipment, the C-shaped cross-section installation member 2, with cylindrical installation hole 2a is utilized. Furthermore, this installation member 2 is constructed using materials of high elasticity, such as synthetic resins. Cylindrical body 17 with stopper 17a is fit on both ends in the axial direction. In this execution example, dentistry drilling machine 1 is installed with free axial rotating movement with respect to installation member 2, by fitting installation hole 2a of installation member 2 on the outer surface of the body of cylindrical body 17, using the elasticity in the circular direction. FIGS. 34 and 35 show execution example 8. In this execution example, separate member 20 is installed in base part 1a through contact part 19 which can be a rotary joint, and dentistry drilling machine 1 is constructed with free axial rotating movement with respect to separate member 20. Inside separate part 20, an induction pipe (not shown in the figure) is installed to introduce air, etc., for the high-speed rotation of cutting tool (bur) 1c. Installation member 2, with the construction shown in FIG. 5, can be installed on the outer surface of the previously mentioned separate member 20. Base part of arm 3 is installed in this installation member 2. Displacement plate 4, with appropriate shape, is installed on the tip of arm 3. It is fixed in a constant position, so that dentistry drilling machine 1 can rotate in the axial direction. FIG. 36 shows execution example 9, with an inner tube used to compensate the tapered surface. In the displacement equipment of execution example 10, as shown in FIGS. 37 through 42, installation hole 2a of installation member 2 is loosely inserted into base part 1a of dentistry drilling machine 1, so as to form gap G. Metallic or plastic stopper 12. 12, with C-shaped or ring-shaped cross section, is installed in both sides of installation member 2.

A straight-line ring-shaped member, with the tip slightly curved towards cutting tool (bur) 1c is used in arm 3, installed in installation hole 2b of installation member 2, mentioned before. Displacement plate 4 is installed, equipped with a circular mirror surface on the tip. In this construction, it is possible to utilize the mirror technique for remote cutting of the 8th upper molar.

In the displacement equipment of execution example 11, shown in FIGS. 43 through 46, installation member 2 is formed as a ring, and installation hole 2a of installation member 2 is loosely installed in base part 1a of dentistry drilling machine 1, so that gap G is formed. Furthermore, stopper 12. 12, formed by members with C-shaped or ring-shaped cross section, is fixed in both sides of installation member 2 of dentistry drilling machine 1. As to the shape of installation member 2, mentioned above, approximately circular ring-shaped or approximately elliptical ring-shaped members can be used.

Figure 48:
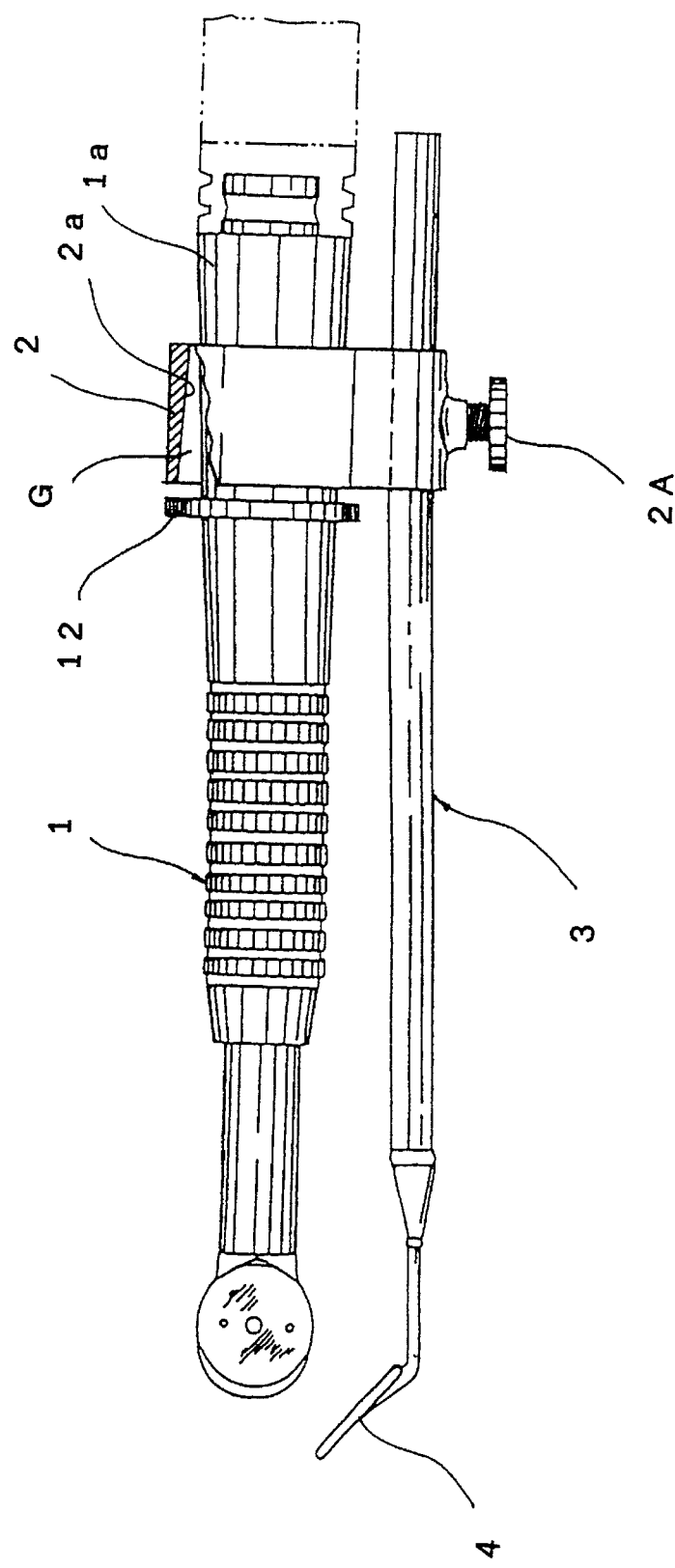
Figure 49:
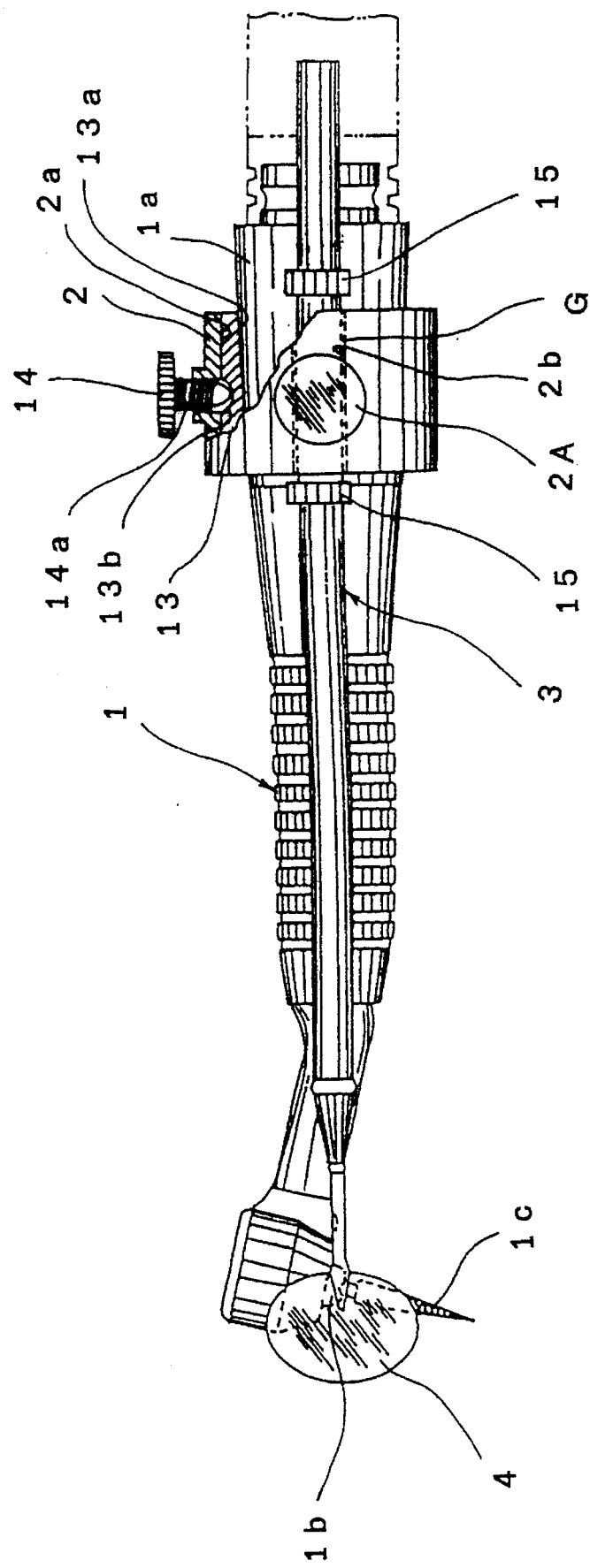
Figure 50:
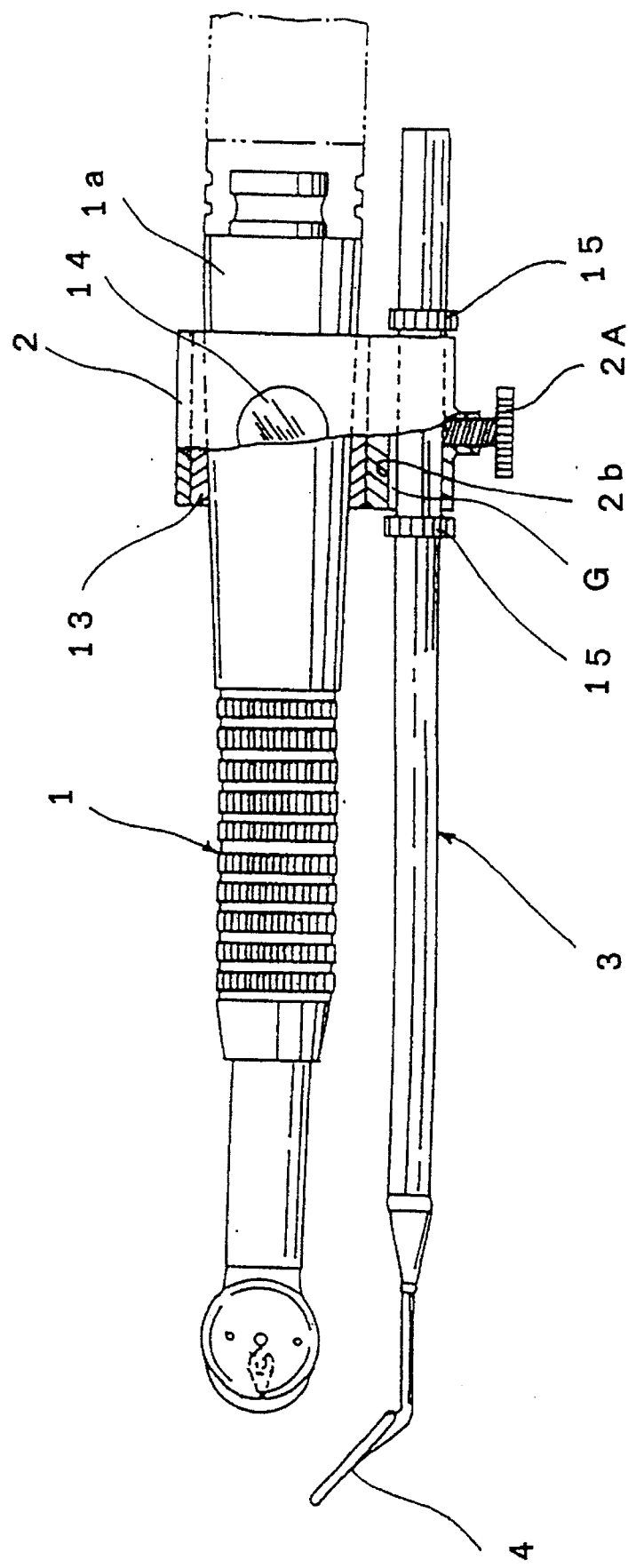

FIGS. 48 and 49 show execution example 13. In this displacement equipment, a small gap G is provided in supporting hole 2b of installation member 2, an arm 3 can be freely installed. For this reason, arm 3 and dentistry drilling machine 1 can do the same movements as described in execution example 1 to 3. However, in FIG. 15. 15, arm 3 is a stopper fixed on the outer surface of arm 3, so that arm 3 cannot separate from supporting hole 2b.

Movement of the Dentistry drilling Machine Inside the Oral Cavity

Figure 53:
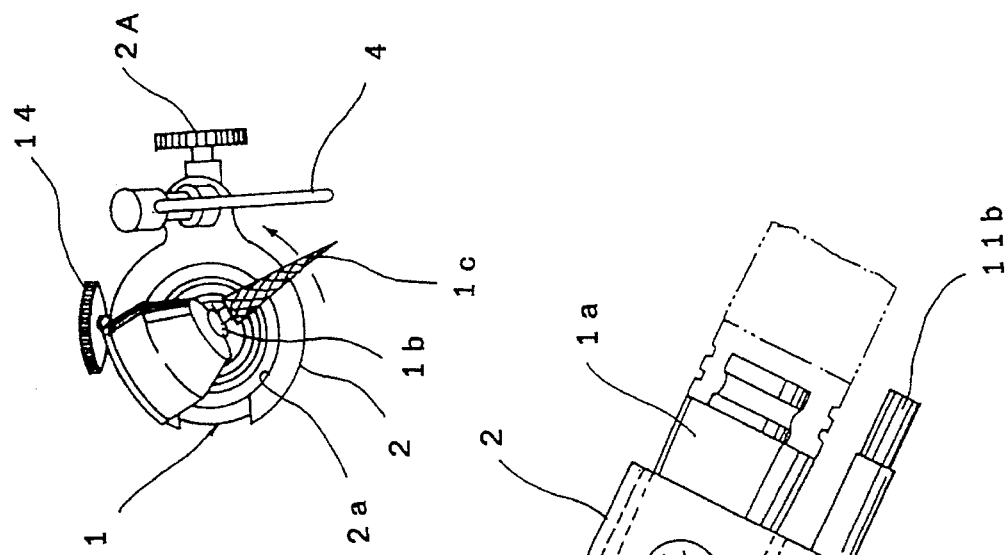
Figure 52:
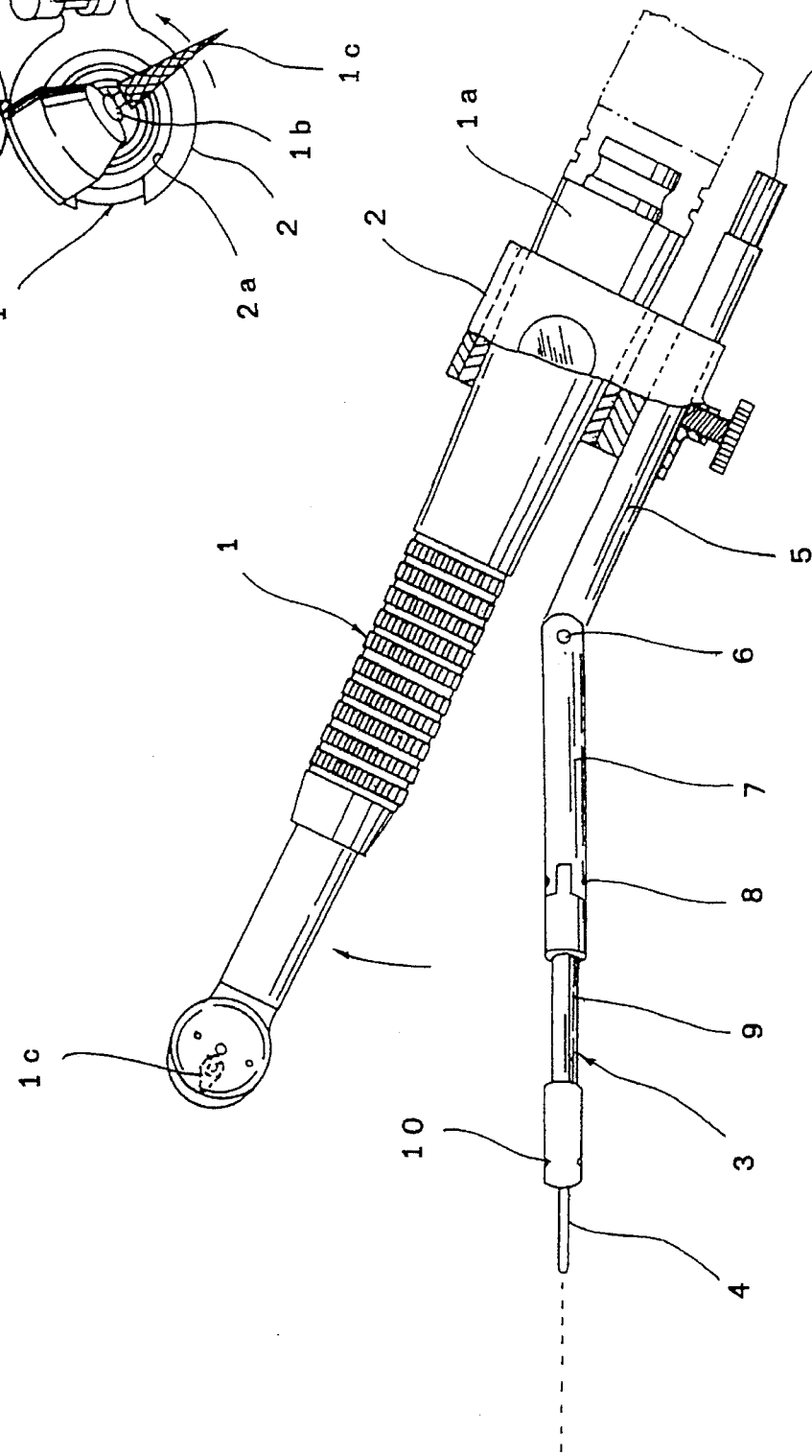
Figure 54:
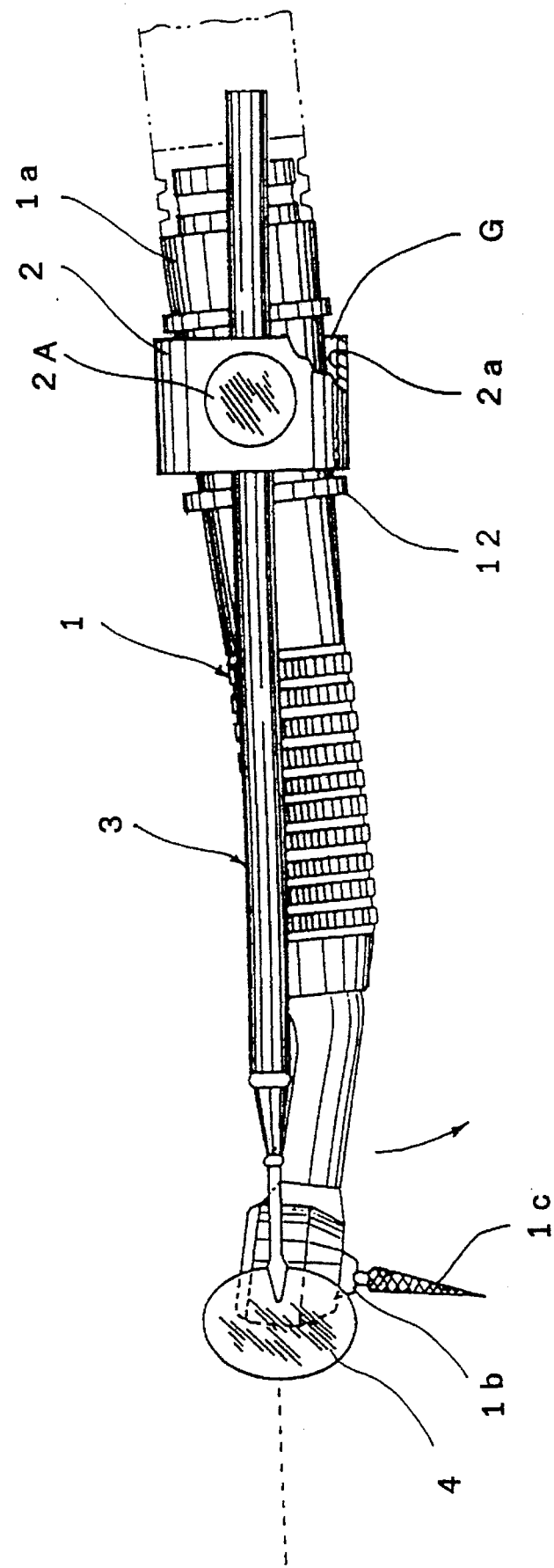
Figure 55:
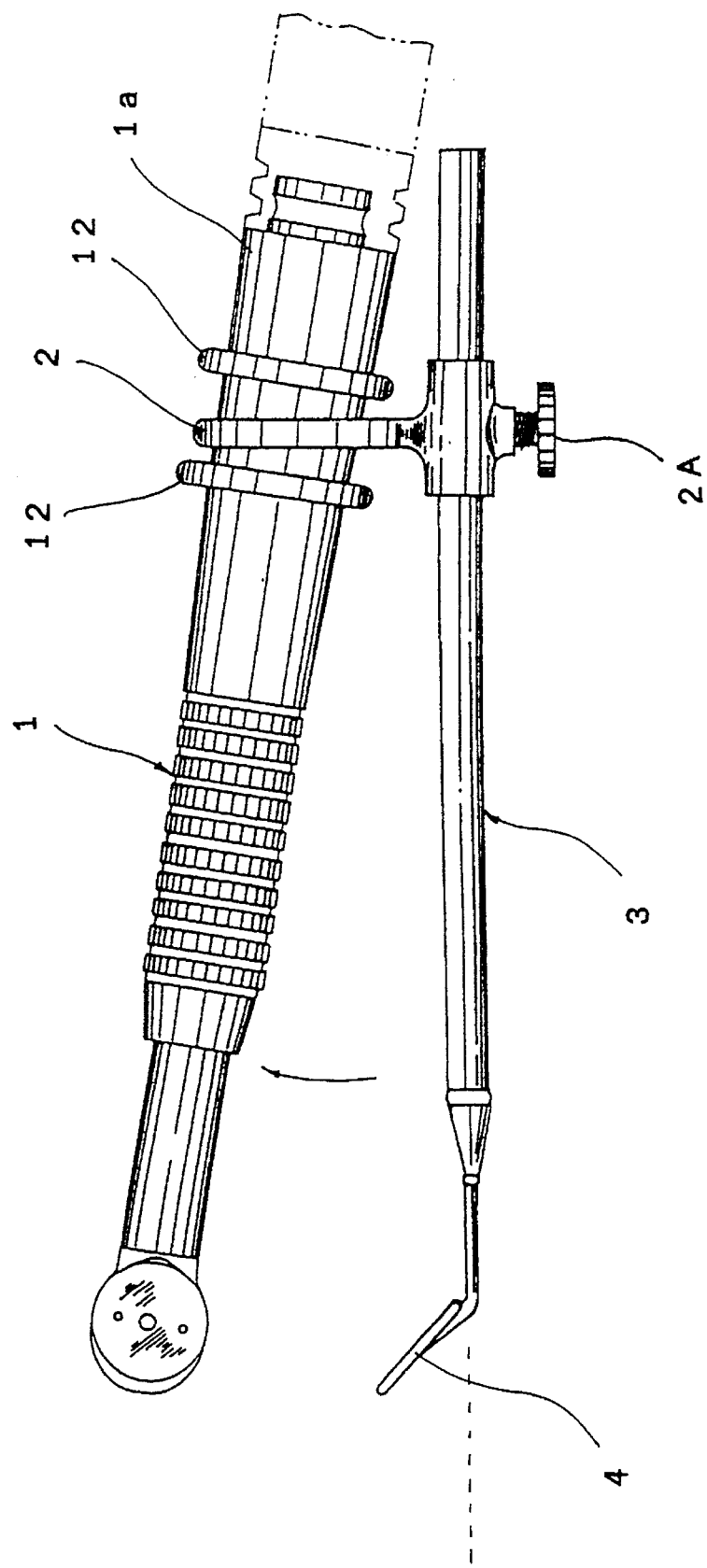

In the construction of the displacement equipment mentioned above, considering that specific oral cavity organs are held by displacement plate 4: (1) thanks to the utilization of arm 3, formed by supporting arm 5, medium arm 7 and tip arm 9, as shown in FIGS. 51 and 52, it is possible to shake cutting tool (bur) 1c in the vertical or horizontal direction and the tip of cutting machine 1 for pressure dentistry. (2) If the construction of dentistry drilling machine 1 permits axial rotation, as shown in FIG. 53, it is possible to rotate cutting tool (bur) 1 around an axis, with one-hand finger operations. (3) If a gap G is formed between the outer surface of the already-mentioned dentistry drilling machine 1 and installation hole 2a of installation member 2, and between stopper 12 and the surface beside installation member 2, as shown in FIGS. 54 and 55, dentistry drilling machine 1 floats with respect to installation member 2. Displacement plate 4 and cutting tool (bur) 1c do open-and-shut movement supported by various points of the rotating position of installation member 2. Thus, cutting tool (bur) 1c moves with considerable freedom, which brings advantages for shape changes of the cutting tool (bur) in small spaces. FIG. 54 shows displacement plate 4 fixed in a constant position and cutting tool (bur) 1c moving in the vertical direction. FIG. 55 shows displacement plate 4 fixed in a constant position and cutting tool (bur) 1c moving in the horizontal direction. Other movements can be easily inferred from the figures.

Figure 56:
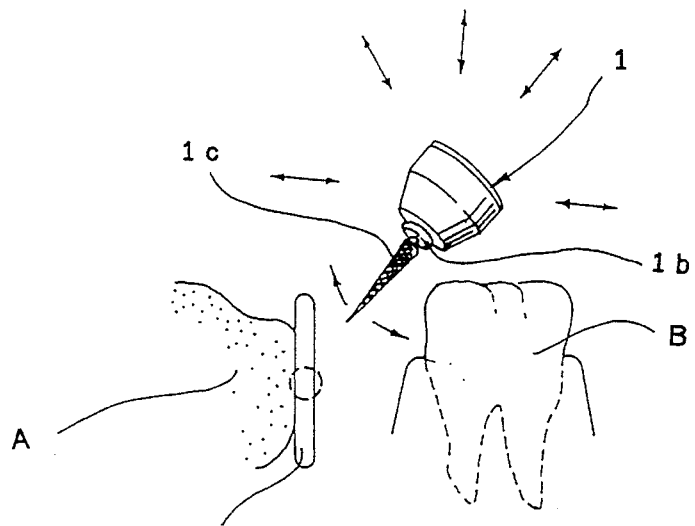
Figure 57:
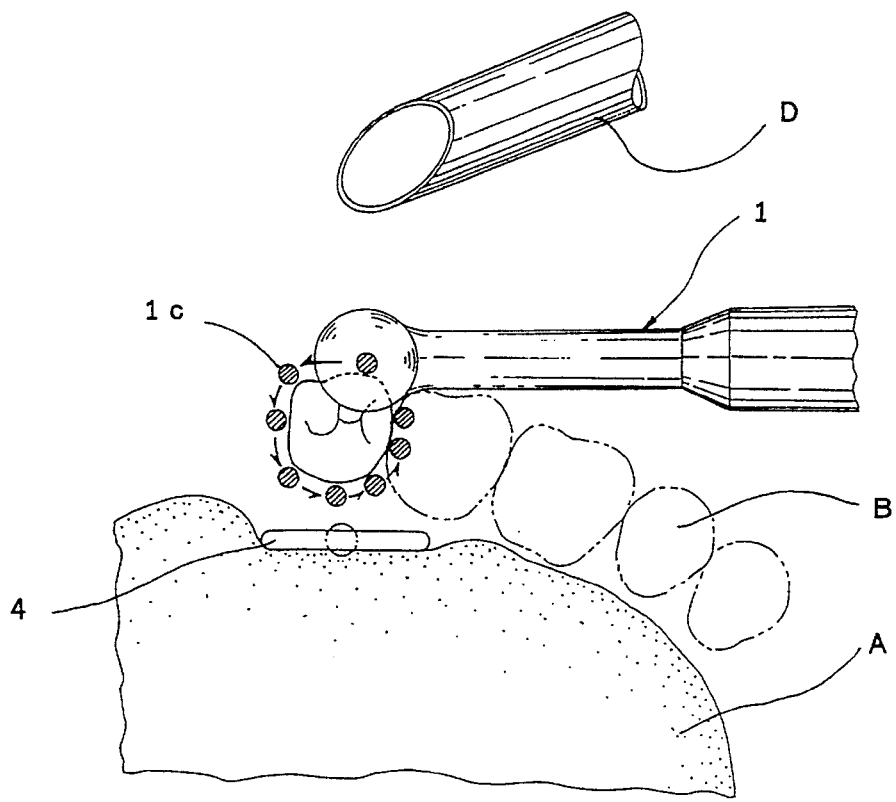
Figure 58:
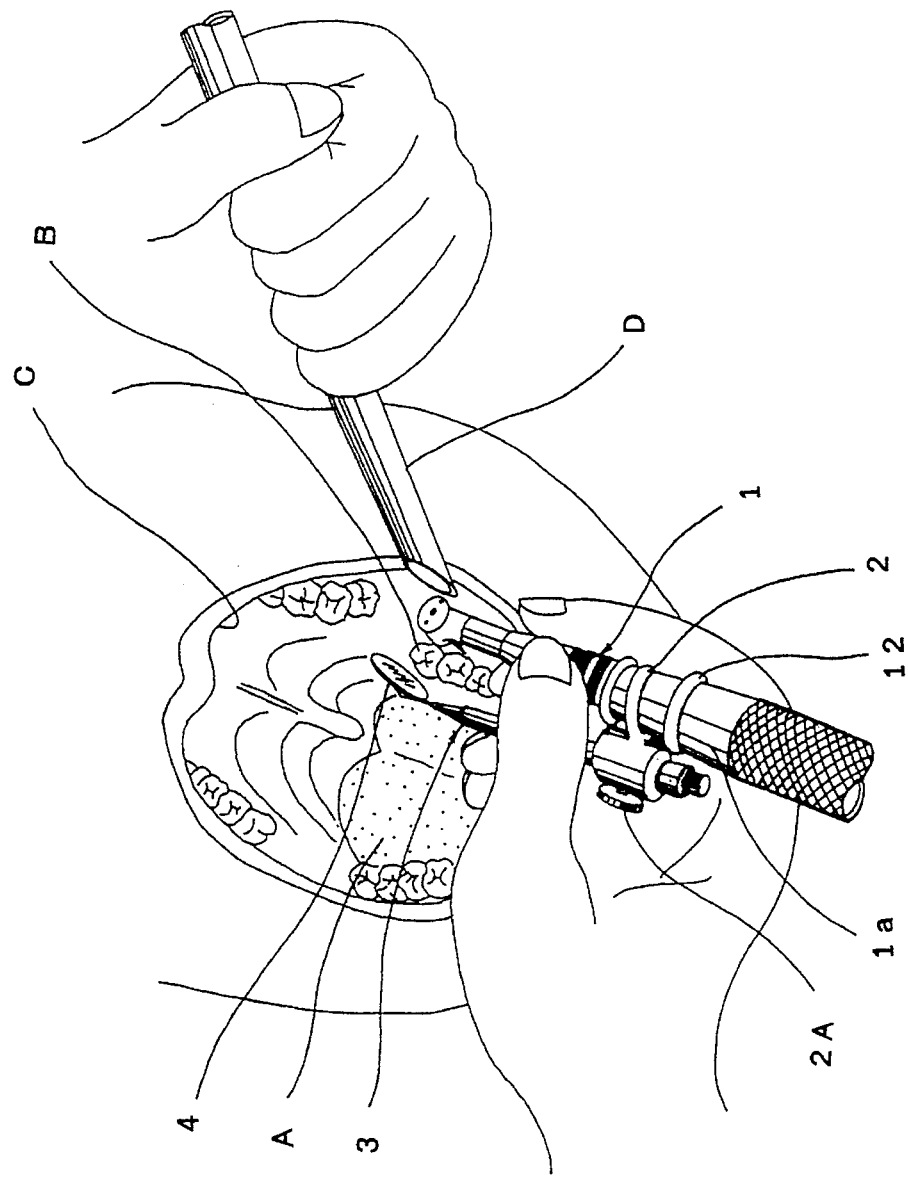
FIGS. 58 to 61 are the schematics explaining the utilization of the displacement equipment.
Figure 59A:
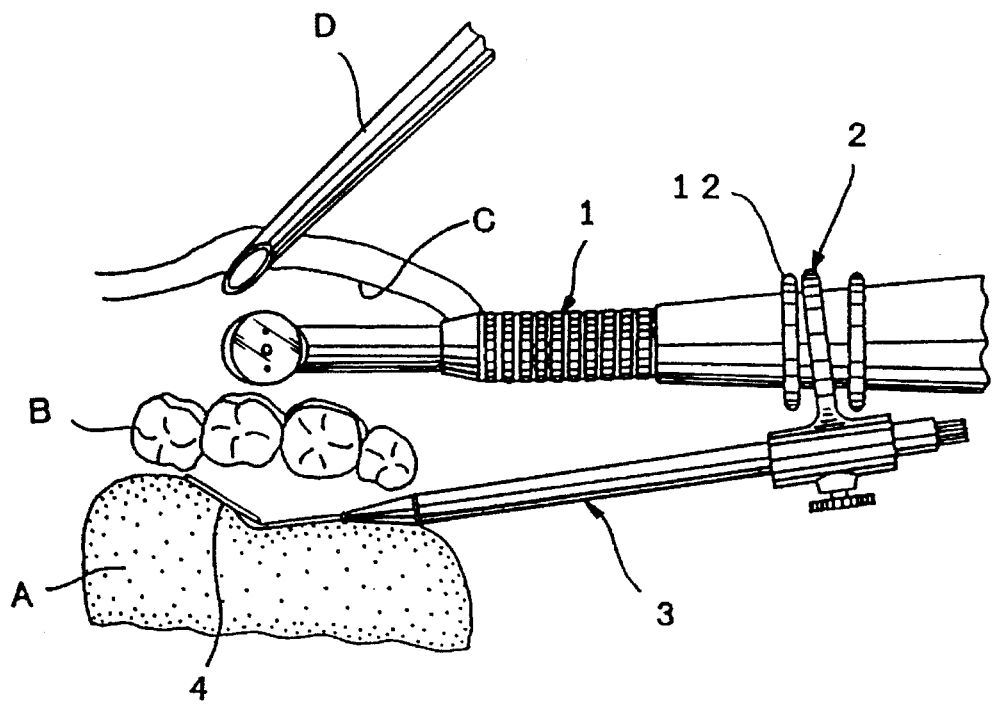
Figure 59B:
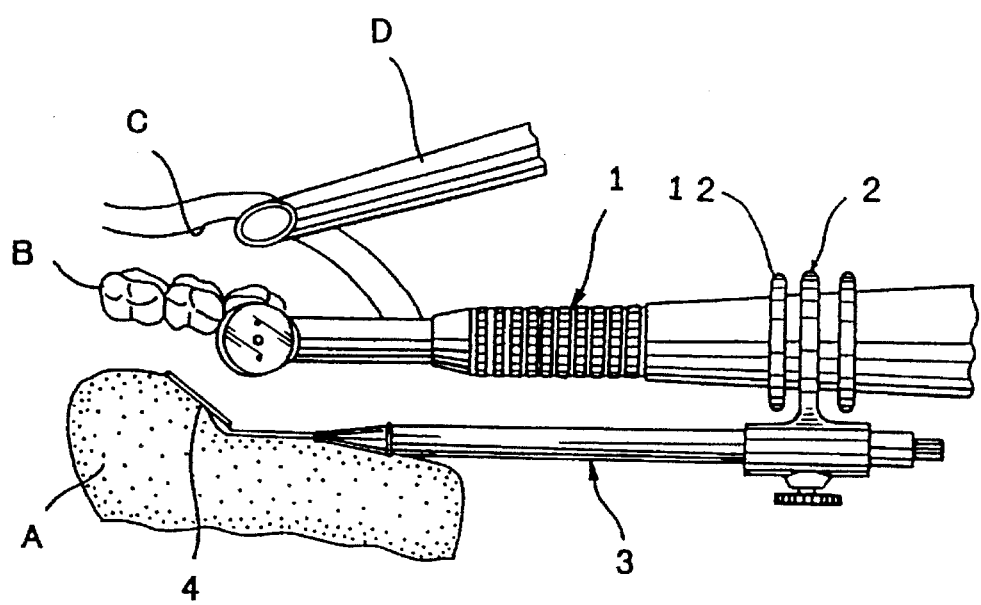
Figure 60A:
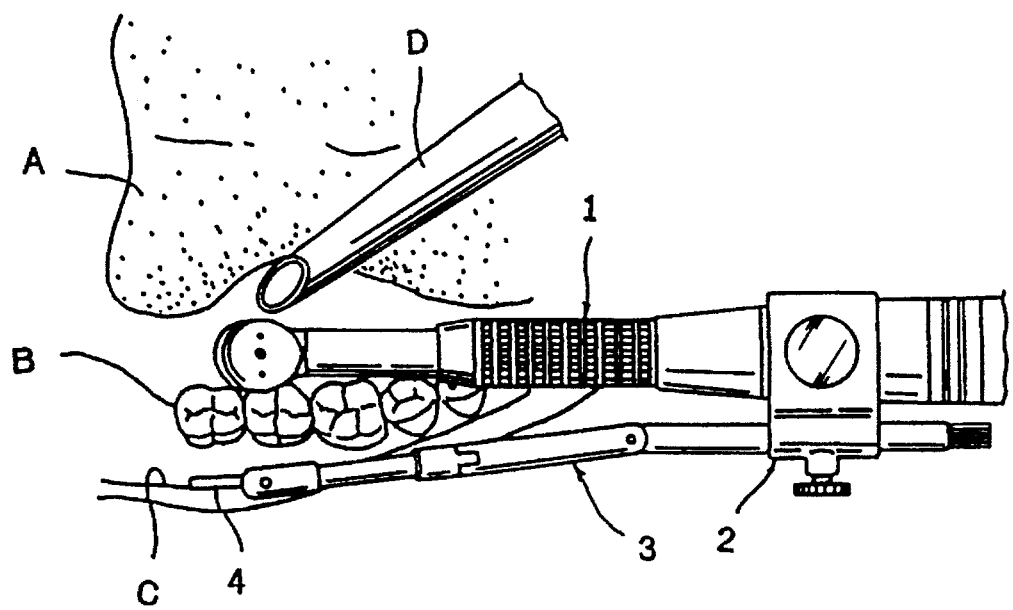
Figure 60B:
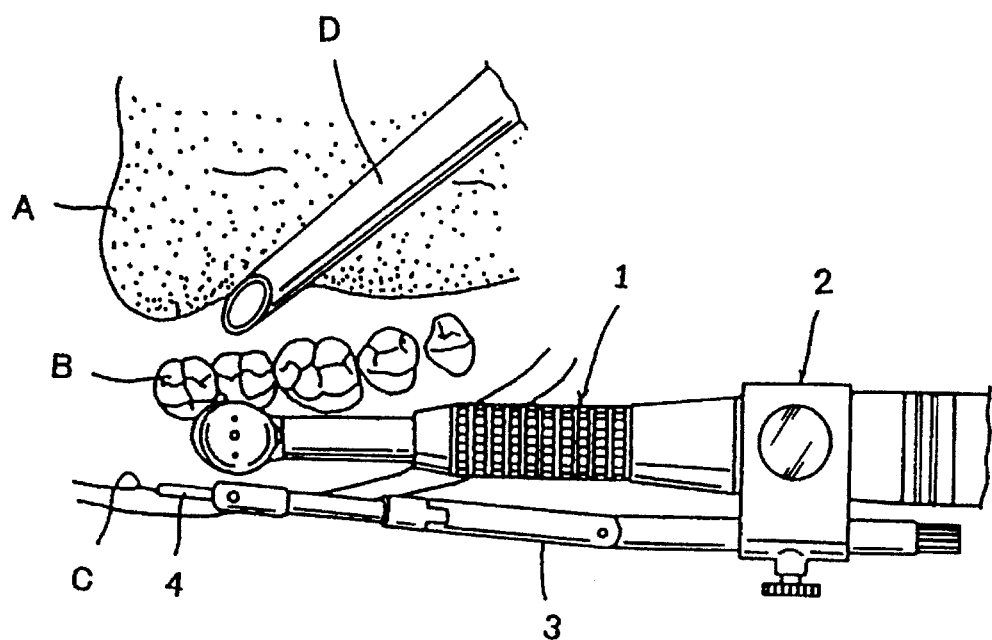
Figure 61:
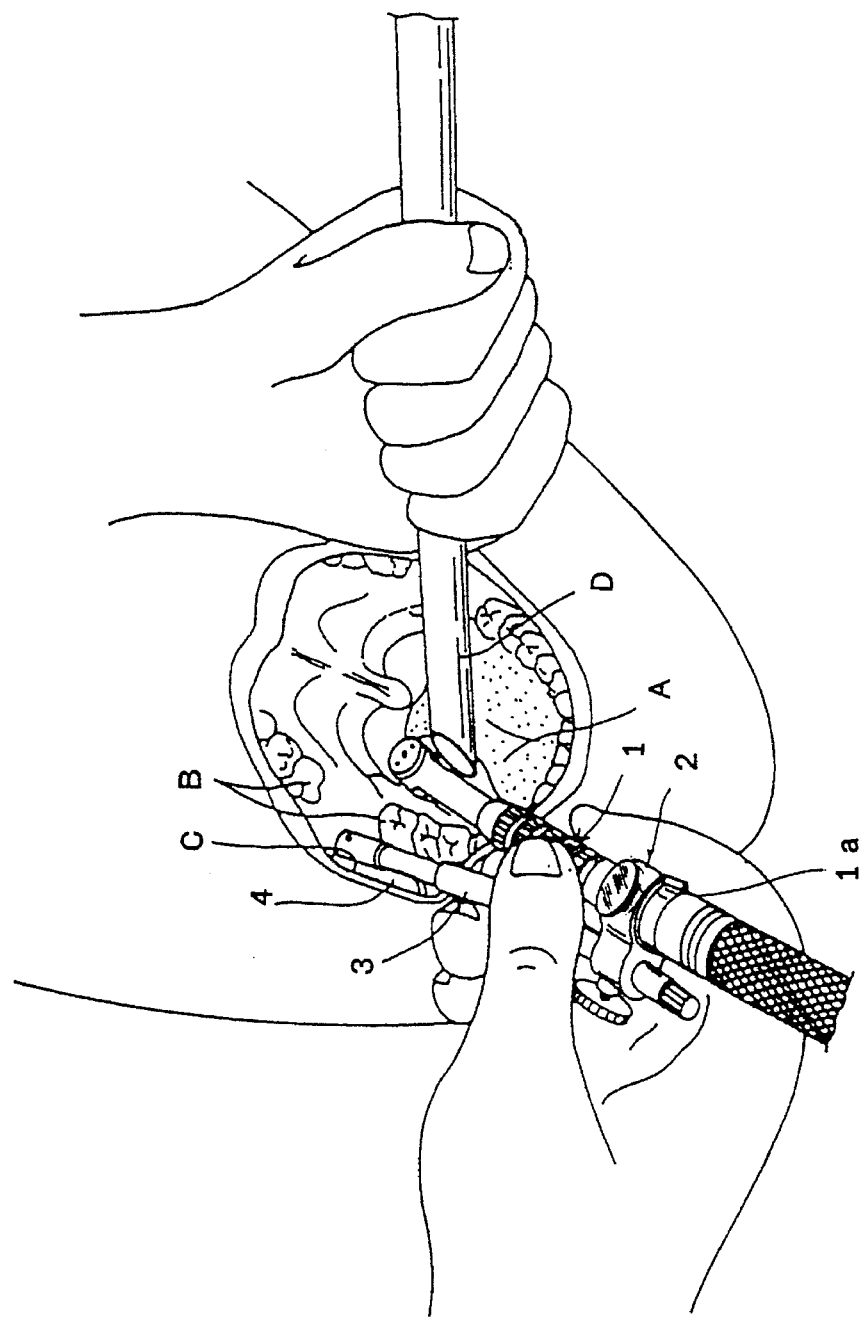
Figure 62A:
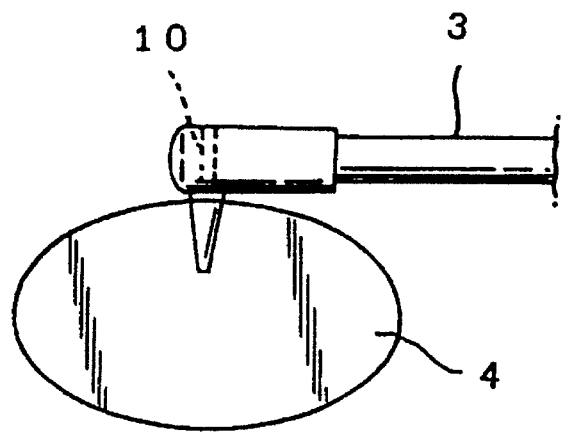
FIGS. 62 to 63 are the sketches of the displacement plate.
Figure 62B:
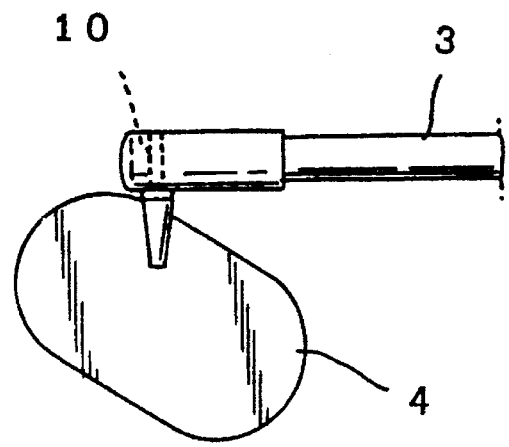
Figure 62C:
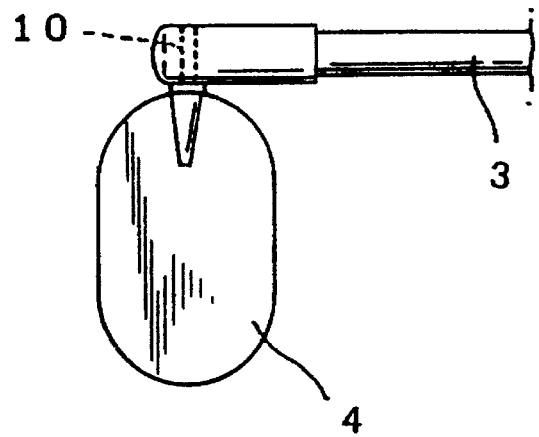
Figure 63C:
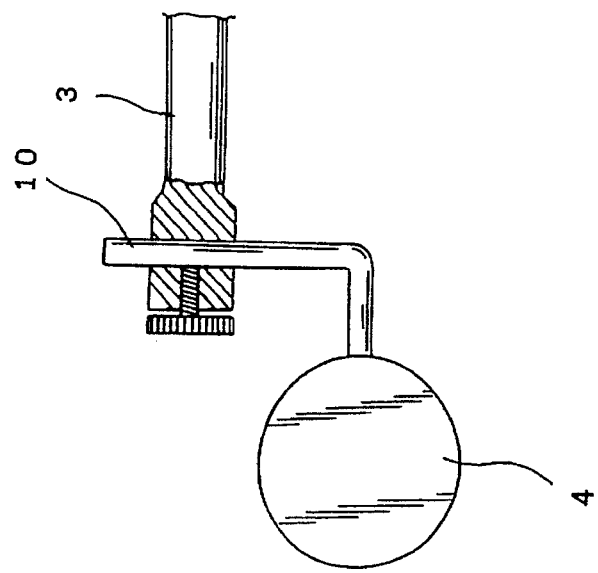
Figure 63B:
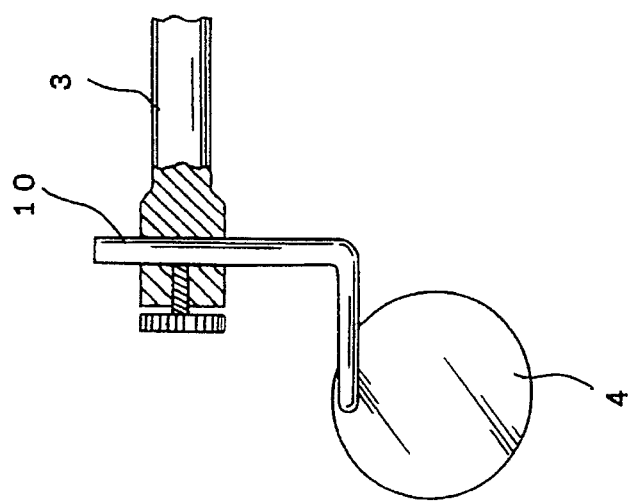
Figure 63A:
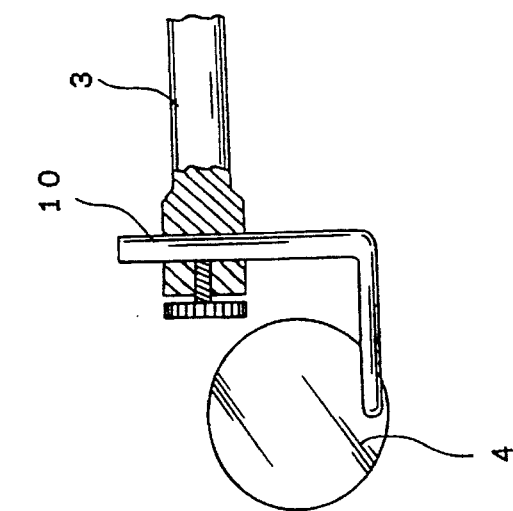

FIGS. 56 and 57 are figures explaining the displacement equipment used in the oral cavity, observed from the ground and side plans. It can be easily observed from the figures that oral cavity organs such as tongue A can be held with displacement plate 4, and cutting tool (bur) 1c can move freely near tooth B.

Method of Utilization of the Displacement Equipment

During treatment, as shown in FIGS. 58 through 61, the dentist holds dentistry drilling machine 1 and the displacement equipment with one hand, and vacuum tip D with the other. In the treatment location, while removing oral cavity organs such as tongue A and flesh part C outside tooth B with vacuum tip D and displacement plate 4, he handles the tip of dentistry drilling machine I with his fingers. It can used in the same manner in various types of treatment, in both upper and lower maxi 11 as.

Other Execution Examples

Figure 64:
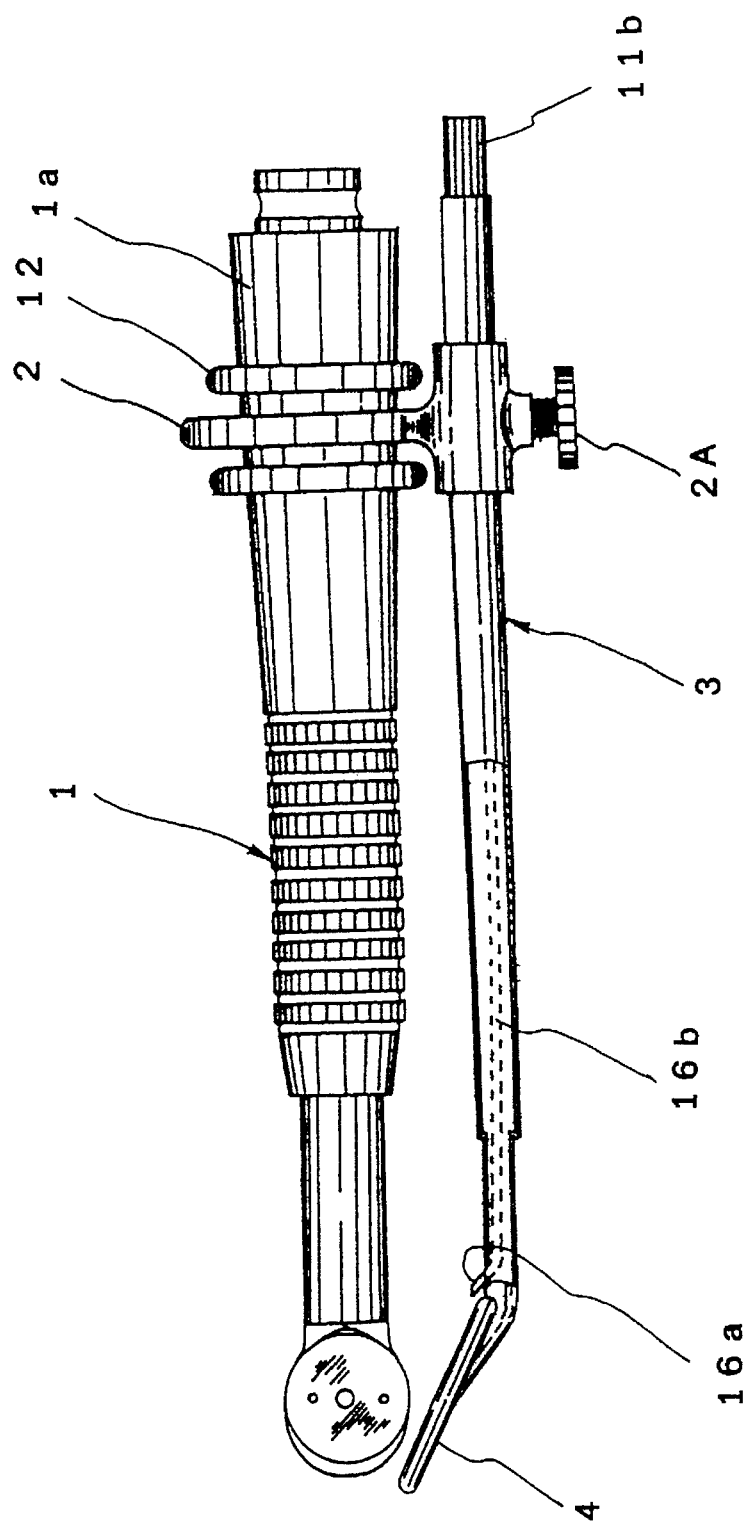
FIG. 64 is the schematics explaining an arm equipped with the jet mechanism.
Figure 65:
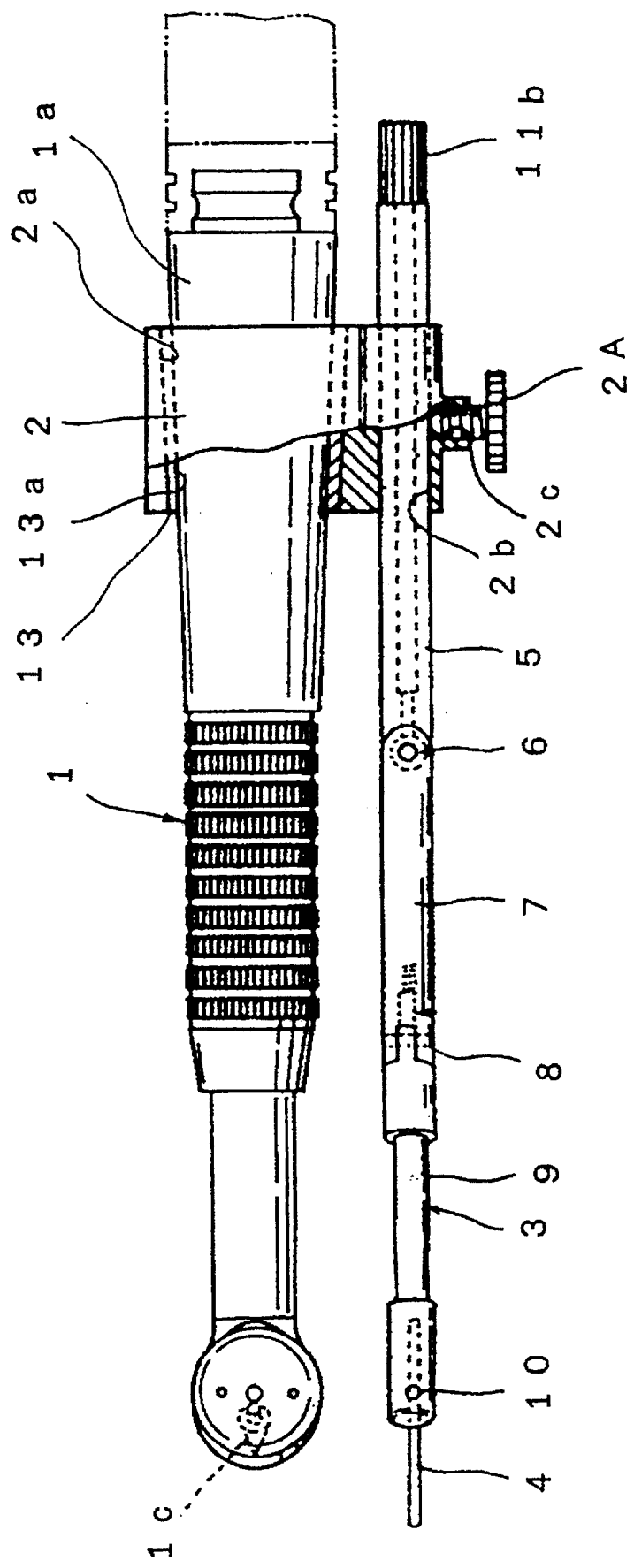
FIG. 65 and 66 are the sketches of the displacement equipment of the other example.
Figure 66:
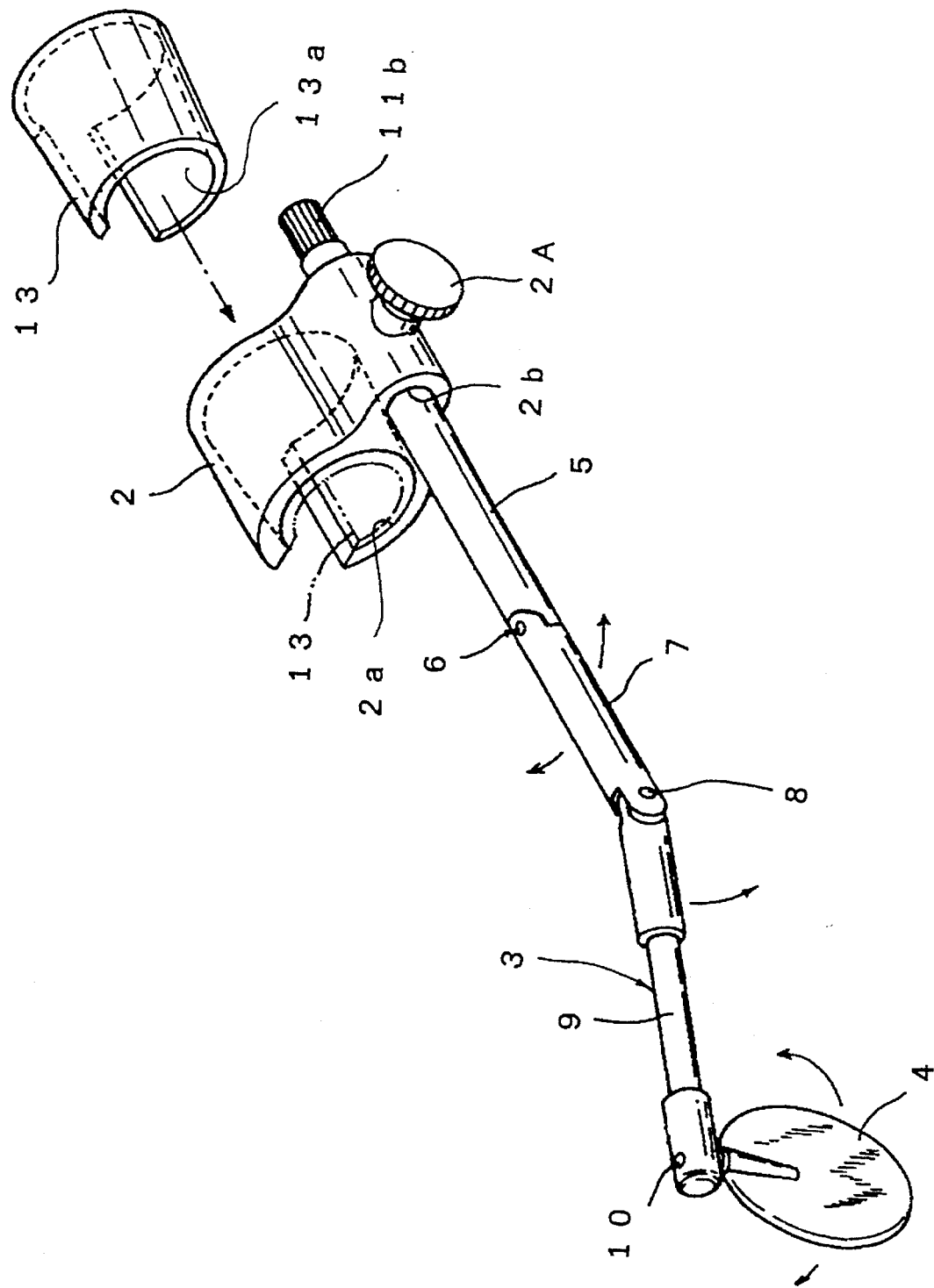
Figure 67:
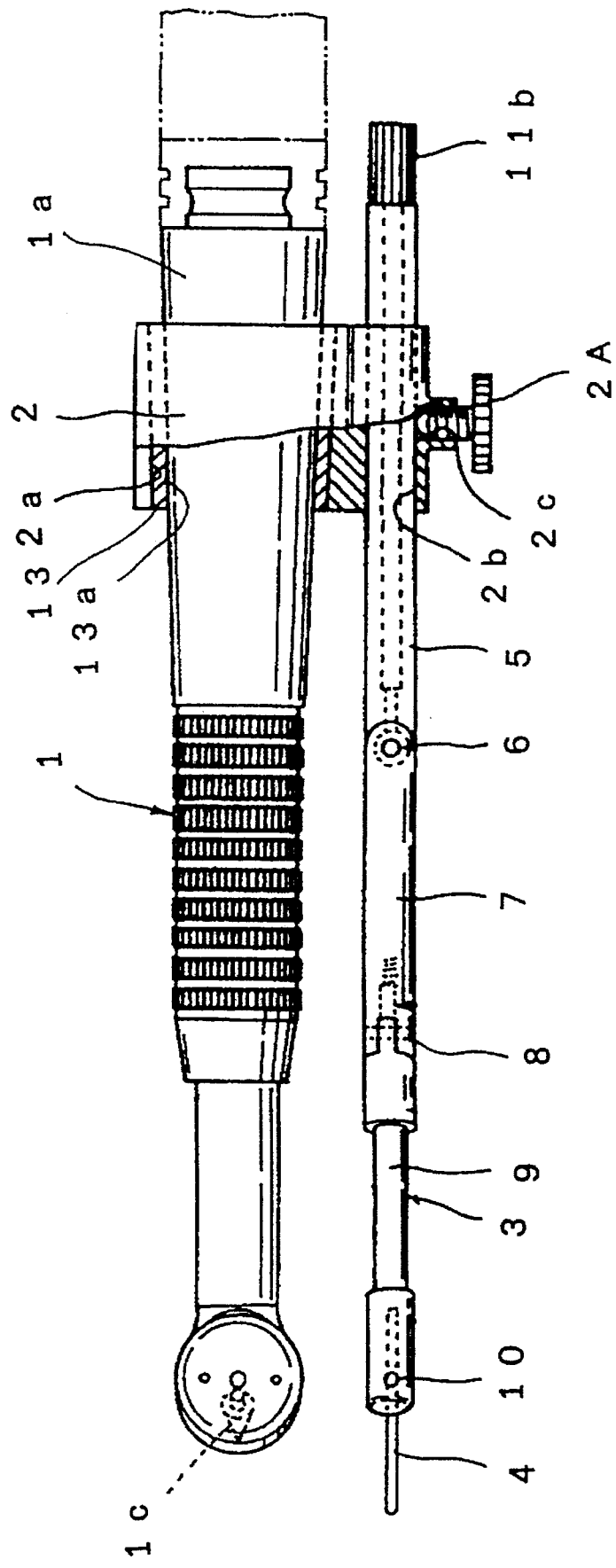
FIG. 67 and 68 are the sketches of the displacement equipment of the other example.
Figure 68:
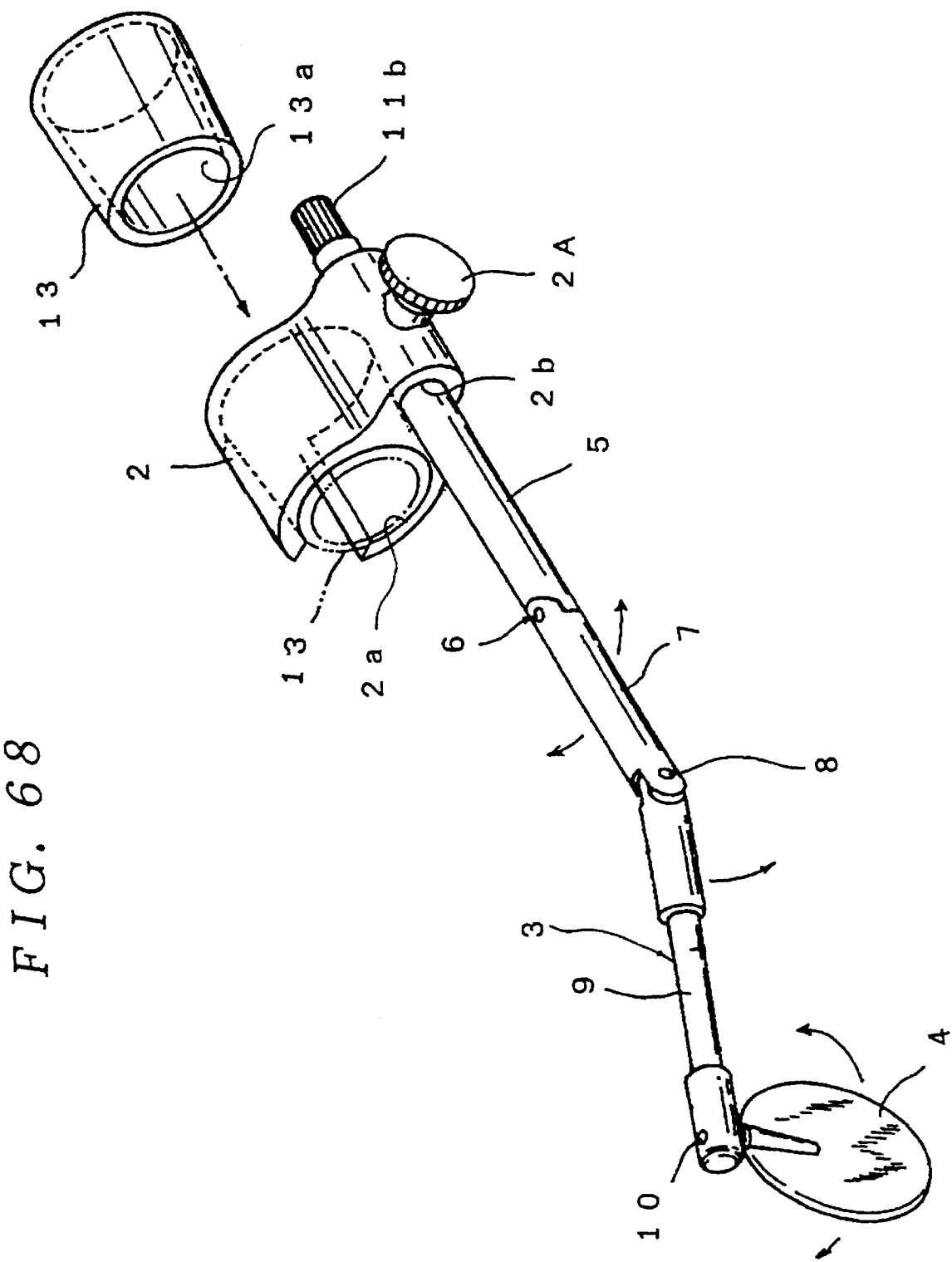
Figure 69:
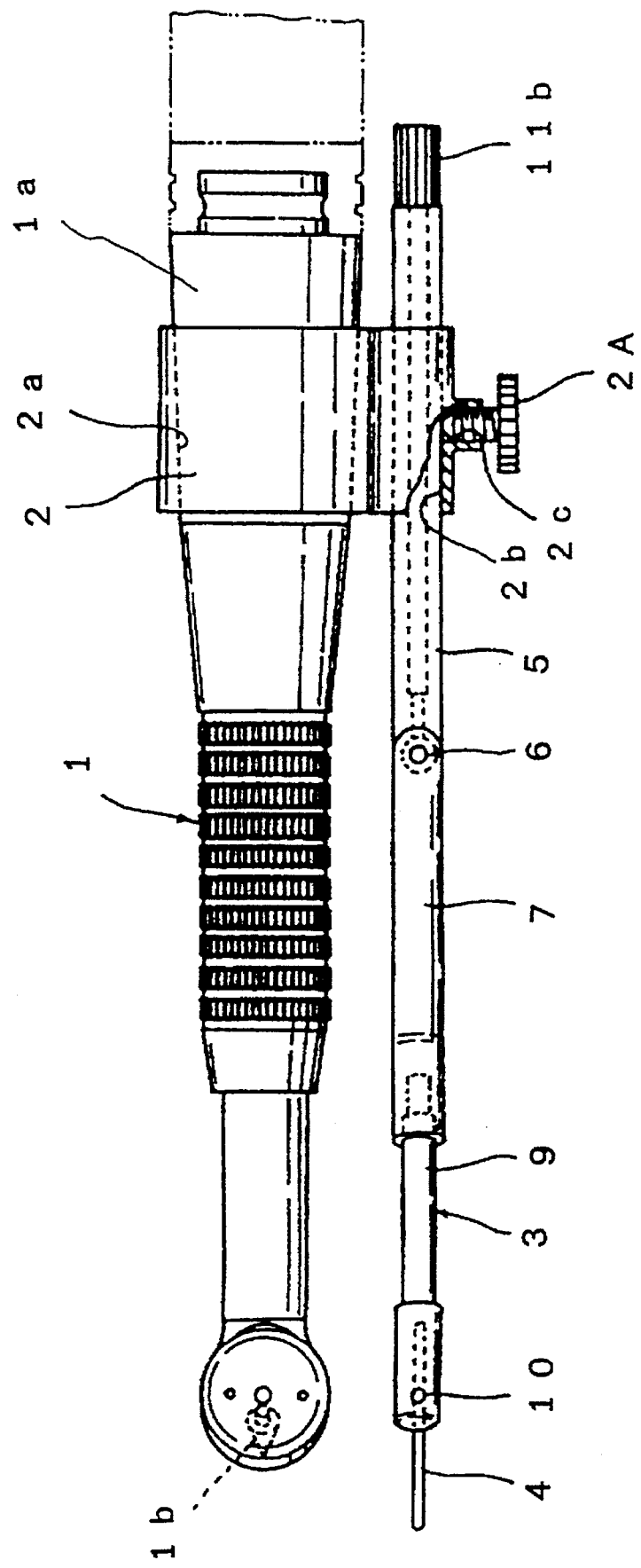
FIG. 69 and 70 are the sketches of the displacement equipment of the other example.
Figure 70:
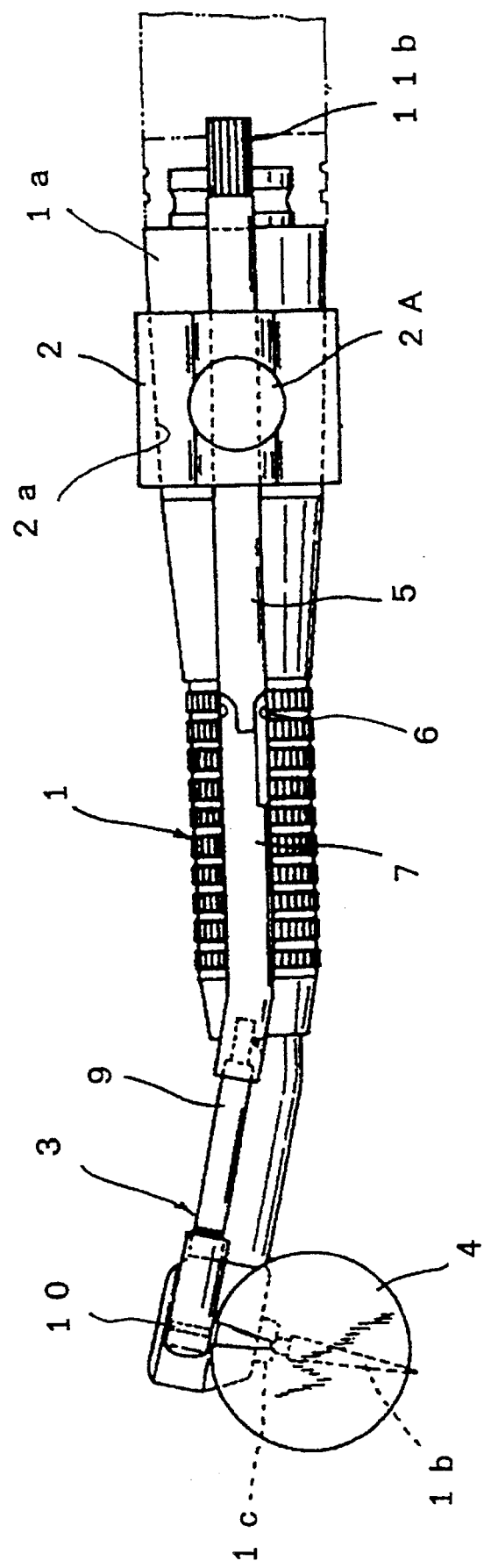

In the case of the execution example in which a mirror is constructed on displacement plate 4 for centrifugal cutting, as shown in FIG. 64, a jet mechanism that blows a jet of air onto displacement plate 4 is constructed. For example, the jet equipment can be formed by jet nozzle 16a, installed on the tip of the approximately straight and pipe-shaped arm 3, by air supplier 16b inside arm 3, and the air supplying equipment not shown in the figure.

I claim:

1. Displacement equipment, for use with dentistry drilling machines to hold oral cavity organs out of the way of the drilling machine, comprising an installation member having a hole into which a base of a dentistry drilling machine is inserted, an arm installed in the installation member, said arm having a tip end, and a displacement plate installed on the tip end of the arm, said displacement equipment further comprising stoppers to prevent the dentistry drilling machine from falling out in an axial direction of said installation hole.

2. Displacement equipment according to claim 1 further including an internal air supplying channel provided in said arm, and a jet nozzle coupled to the air channel and located on the tip of the arm in front of the displacement plate.

3. A displacement equipment according to claim 2 wherein said displacement plate comprises a mirror.

4. Displacement equipment for use with, dentistry drilling machines to hold oral cavity organs out of the way of the drilling machine, comprising an installation member with an installation hole into which a base of a dentistry drilling machine is inserted, an arm installed in the installation member said arm having a tip end and a rotating mechanism, and a displacement plate installed on the tip of the arm through said rotating mechanism, said displacement plate comprising at least two different tongue shapes which can be selected by rotating the displacement plate depending on the shape of the oral cavity organs and stoppers installed in said installation hole to prevent the dentistry drilling machine form falling out in an axial direction of said installation hole.

5. Displacement equipment for use with a dentistry drilling machine, said displacement equipment comprising an installation member having an installation hole into which a base of a dentistry drilling machine is inserted, an arm installed in the installation member, said arm having a tip and a displacement plate installed on the tip of the arm, a supporting arm member installed in the installation member, a medium arm member, a horizontal rotating mechanism for installing said medium arm member on the supporting arm member, a tip arm member, a vertical rotating mechanism for installing said tip arm member on the medium arm member and stoppers installed in said installation hole to prevent the base of dentistry drilling machine from falling out in an axial direction of the installation hole.

6. Displacement equipment for use with dentistry drilling machines to hold oral cavity organs out of the way of the drilling machine comprising an installation member having an installation hole into which a base of dentistry drilling machine is inserted, an arm installed in the installation member, said arm having a tip, and a displacement plate installed on the tip of the arm, said arm being formed at least by a first arm member installed in the installation member, and a second arm member, a horizontal rotating mechanism for installing said second arm member on the first arm member and an adjustment means coupled between the first and second arm members to maintain the first arm member at a fixed angle with respect to the second arm member, and stoppers installed in said installation hole to prevent the base of the dentistry drilling machine from falling in and out in an axial direction of the installation hole.

* * * * *

UNITED STATES PATENT AND TRADEMARK OFFICE
CERTIFICATE OF CORRECTION

PATENT NO.   : 5,607,303
DATED        : March 4, 1997
INVENTOR(S)  : Shoukou Nakamura It is certified that error appears in the above-identified patent and that said Letters Patent is hereby corrected as shown below:

Item [30] Foreign Application Priority Data:

Add --August 4, 1993     [JP]   Japan ....... 5-212285
    February 22, 1994    [JP]   Japan ....... 6-47800
    July 27, 1994        [JP]   Japan ....... 6-193869--

Signed and Sealed this

Ninth Day of September, 1997

*Attest:*

BRUCE LEHMAN

*Attesting Officer*     Commissioner of Patents and Trademarks